(12) United States Patent
Stanise

(10) Patent No.: US 12,426,924 B1
(45) Date of Patent: Sep. 30, 2025

(54) DEVICE AND METHOD FOR TREATING DERMATITIS, PSORIASIS, ACNE AND OTHER DISORDERS OF THE SKIN

(71) Applicant: Elista Laboratories LLC, Boca Raton, FL (US)

(72) Inventor: John Stanise, Boca Raton, FL (US)

(73) Assignee: Elista Laboratories LLC, Boca Raton, FL (US)

( * ) Notice: Subject to any disclaimer, the term of this patent is extended or adjusted under 35 U.S.C. 154(b) by 0 days.

(21) Appl. No.: 19/080,352

(22) Filed: Mar. 14, 2025

(51) Int. Cl.
  *A61B 17/54*  (2006.01)
  *A61B 17/00*  (2006.01)

(52) U.S. Cl.
  CPC .. *A61B 17/545* (2013.01); *A61B 2017/00761* (2013.01); *A61B 2017/00862* (2013.01); *A61B 2217/005* (2013.01)

(58) Field of Classification Search
  CPC .................. A61B 17/54; A61B 17/545; A61B 2017/00761; A61B 2217/005; A61B 2217/007; A61N 5/0616; A61H 9/005; A61H 9/0057; A61H 9/0071; A61H 9/0078; A61H 9/0085; A61H 9/0092; A61H 2009/0064
  See application file for complete search history.

(56) References Cited

U.S. PATENT DOCUMENTS

| 4,114,781 A | 9/1978 | Doyel |
| 7,572,238 B2 | 8/2009 | Rhoades |
| 7,762,965 B2 | 7/2010 | Slatkine |
| 8,518,001 B2 | 8/2013 | Hasenoehrl et al. |
| 8,708,980 B2 | 4/2014 | Welser |
| 8,979,785 B2 | 3/2015 | Korogi et al. |
| 9,950,147 B2 | 4/2018 | Mehta |

(Continued)

FOREIGN PATENT DOCUMENTS

| JP | 2017-171648 A | 9/2017 |
| WO | 2017007939 A1 | 1/2017 |
| WO | 2020259871 A1 | 12/2020 |

OTHER PUBLICATIONS

Machine Translation of Specification for JP 2017-171648 A (2017).

(Continued)

*Primary Examiner* — Diane D Yabut
*Assistant Examiner* — Christian D Knauss
(74) *Attorney, Agent, or Firm* — Caesar Rivise, PC

(57) ABSTRACT

A skin treatment device includes: an elastic enclosure having a hollow center chamber with an opening at a proximal end thereof; a lip around a perimeter of the opening; protrusions and channels on the lip, which selectively: (i) permit expulsion of air and water from the chamber during initial compression of the device against the skin; (ii) terminate the flow of air and water from the chamber when the lip has been sufficiently compressed against the skin to form a seal between the lip and skin; and (iii) permit air to enter the chamber upon decompression of the device and breaking the seal; and at least one outlet valve on the enclosure configured to permit an additional flow of air and water out of the chamber during compression and to resist admission of air or water into the chamber during decompression. A skin treatment method is also disclosed.

28 Claims, 24 Drawing Sheets
(7 of 24 Drawing Sheet(s) Filed in Color)

(56) References Cited

U.S. PATENT DOCUMENTS

| | | | |
|---|---|---|---|
| 10,252,044 | B2 | 4/2019 | Bock |
| 10,369,073 | B2 | 8/2019 | Rosario et al. |
| 10,524,835 | B2 | 1/2020 | Shadduck et al. |
| 10,568,759 | B2 | 2/2020 | Yee et al. |
| 10,765,552 | B2 | 9/2020 | Root et al. |
| 10,799,430 | B2 | 10/2020 | Danto |
| 11,241,357 | B2 * | 2/2022 | Ignon ............... A61P 17/06 |
| 12,193,619 | B1 | 1/2025 | Lane |
| 2002/0165220 | A1 | 11/2002 | Heesch |
| 2009/0156982 | A1 | 6/2009 | Petrie et al. |
| 2014/0323993 | A1 | 10/2014 | Wilcox et al. |
| 2015/0026902 | A1 | 1/2015 | Berglund |
| 2016/0000646 | A1 | 1/2016 | Scherkowski |
| 2016/0022009 | A1 | 1/2016 | Rabe et al. |
| 2018/0264245 | A1 | 9/2018 | Edwards et al. |
| 2018/0361437 | A1 | 12/2018 | Jansen et al. |
| 2020/0009007 | A1 | 1/2020 | Shadduck |
| 2021/0298540 | A1 | 9/2021 | Smith et al. |
| 2022/0211167 | A1 | 7/2022 | Wang et al. |
| 2024/0099449 | A1 | 3/2024 | Braden |

OTHER PUBLICATIONS

Armstrong et al. Psoriasis Prevalence in Adults in the United States. JAMA Dermatol. 2021; 157(8):940-946.
Clark et al. Diagnosis and treatment of seborrheic dermatitis. American Family Physician, 2015; 91(3):185-190.
Piquero-Casals et al. Topical non-pharmacological treatment for facial seborrheic dermatitis. Dermatol Ther. 2019;9:469-477.

* cited by examiner

FIG. 7A
FIG. 7B
FIG. 7C
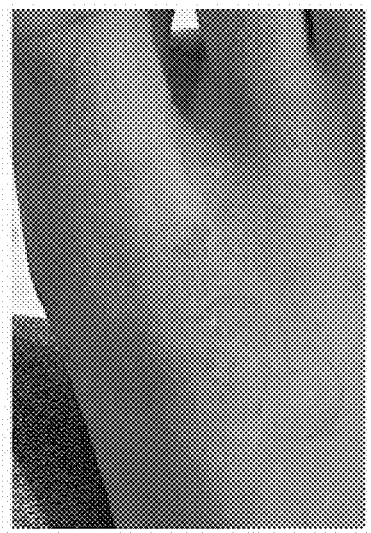
FIG. 8A
FIG. 8B
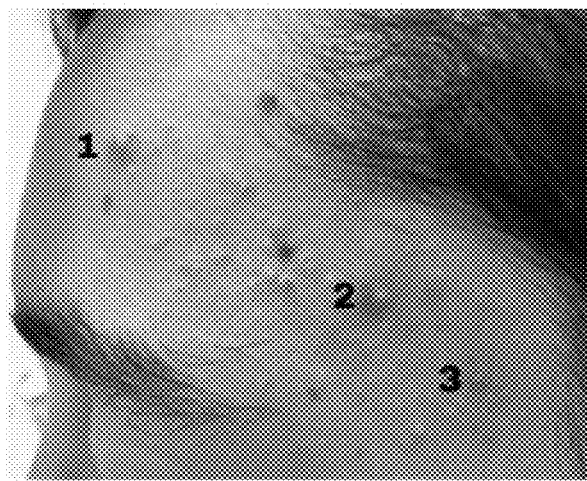
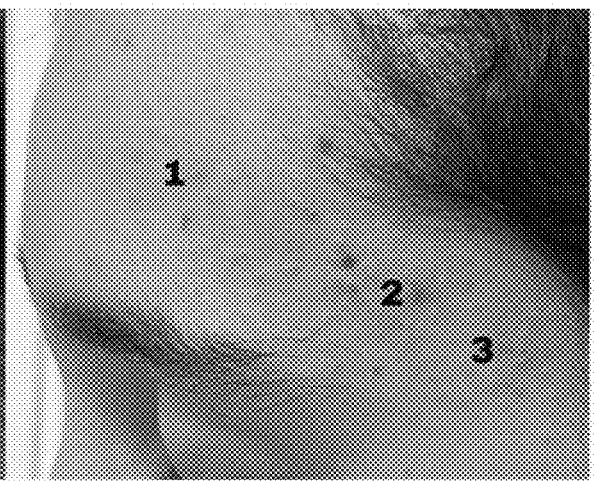

DEVICE AND METHOD FOR TREATING DERMATITIS, PSORIASIS, ACNE AND OTHER DISORDERS OF THE SKIN

BACKGROUND OF THE INVENTION

1. Field of Invention

This invention relates to the treatment of skin disorders and more particularly to a device and method for treating dermatitis, psoriasis, eczema, acne and/or other skin disorders.

2. Description of Related Art

Dermatitis is a general term for skin inflammation, which can have various causes and manifestations. Dermatitis can affect any part of the body and cause symptoms such as redness, itching, dryness, scaling, blistering, cracking, and oozing. Dermatitis can also impair the skin barrier function and increase the risk of skin infections and allergic sensitization. There are several different types of dermatitis, including but not limited to atopic dermatitis and seborrheic dermatitis.

Atopic dermatitis (or eczema) is the most common form of dermatitis. Symptoms of atopic dermatitis vary but typically include discolored dry skin patches, which may be scaly and/or accompanied by raised fluid-filled bumps.

Seborrheic dermatitis is another common form of dermatitis, which can cause flaking of scaly patches of discolored skin. It tends to affect oily areas of the body, such as the face, scalp, eyebrows, eyelids, ears and chest. There is no known cure for seborrheic dermatitis.

Acne and dermatitis are two skin conditions that can look similar but have different causes and treatments. Acne is caused by the oil glands under the skin, while dermatitis is an autoimmune condition that causes inflammation of the skin.

Psoriasis is an autoimmune disorder in which patches of skin become scaly and inflamed, most often on the scalp, elbows, knees and lower back. It is the one of the most common autoimmune disease in the United States, affecting approximately 7.5 million U.S. adults according to Armstrong et al. Psoriasis Prevalence in Adults in the United States. JAMA Dermatol. 2021 Aug. 1; 157 (8): 940-946. doi: 10.1001/jamadermatol.2021.2007. PMID: 34190957; PMCID: PMC8246333. There is no known cure for psoriasis.

Treatments for skin conditions vary in complexity and efficacy.

Topical antifungals, such as ketoconazole, selenium sulfide, coal tar and zinc pyrithone, have been used to treat seborrheic dermatitis. Such treatments are most effective for treating the mildest cases of seborrheic dermatitis. Oral antifungals may be prescribed in the most severe cases.

Topical steroids, such as hydrocortisone, and systemic steroids, such as prednisone, have been prescribed to minimize inflammation associated with dermatitis. However, steroids have undesirable side effects, such as headache, nausea, vomiting, acne, thinning skin, weight gain, restlessness and insomnia.

Calcineurin inhibitors, such as tacrolimus and pimecrolimus, have been prescribed for topical application to treat atopic dermatitis. Although these compounds exhibit anti-inflammatory properties without some of the side effects of steroids, they are potentially carcinogenic.

Autoimmune drugs have been used to treat psoriasis, but have significant side effects including but not limited to increased risk of infections, allergic reactions, skin cancers, headaches, flu-like symptoms, and urinary tract infections.

Phototherapy, also known as light therapy, is a treatment method that employs selected wavelengths of ultraviolet light (e.g., UVB light) to manage the symptoms of eczema and/or psoriasis. Over the course of one to two months, consistent phototherapy can lead to noticeable improvement in the symptoms. However, potential side effects include sunburn, skin tenderness, itching, dryness, dark spots, premature skin aging and skin cancer.

Devices for treating dermatitis with or without medications also exist.

For example, U.S. Patent Application Publication No. 20140323993 A1 discloses an applicator for topically applying a semi-solid medicament, which comprises an applicator head having an applicator face for spreading medicament across the skin; a sealable aperture on the applicator face; and a drive mechanism for forcing medicament out through the aperture. The applicator head includes a cartridge port at the rear of the applicator face for receiving a dispensing end of a cartridge charged with medicament. The drive mechanism comprises a dial knob rotatable around a longitudinal axis of the applicator for advancing a piston along a drive member towards the applicator head to force medicament from the cartridge and thereby dispense a predetermined dose of medicament onto the applicator face. See Abstract. Dermatitis is disclosed at Paragraph as a condition that can be treated with the applicator.

WO 2017007939 A1 discloses a device and method of promoting hair growth or hair stimulation. The device applies a vacuum or suction using a handpiece assembly along a targeted portion of the subject's skin surface where hair growth or hair stimulation is desired and provides at least one treatment material to said targeted portion of the subject's skin surface. In certain embodiments, the device and method are used to treat conditions such as seborrheic dermatitis. See Paragraph [0149].

JP 2017171648 A discloses a device for applying a substance to the scalp. The device comprises a squeezable container having a porous opening through which the substance is applied to the scalp. The application at Paragraph discloses that the device can be used to treat dermatitis of the scalp.

US20150026902 A1 discloses a roller for cleaning the skin comprising a wheel mounted on a handle having means for mounting said wheel, and where the wheel's periphery has asymmetrical suction cups with elongated shapes. Said suction cups have their suction surfaces oriented out from the center axis of the wheel and are preferably made of rubber or elastomer.

US20210298540 A1 discloses a cleansing device including a body, a head, an applicator, and a diaphragm. The body can define a handle. The head can be mechanically coupled to the body. The applicator can be arranged on a top of the head. The applicator can include an application surface and a back surface, and can define a plurality of openings. The diaphragm can be disposed within the head and against the back surface of the applicator. The diaphragm is configured to move in a reciprocating manner towards and away from the back surface of the applicator to create a suction force within the plurality of openings configured to draw contaminates away from pores of a cleansable surface that abuts the application surface of the applicator.

US20220211167 A1 (Wang) discloses an automatic suction cleaning structure disposed on a cleaner body. The automatic suction cleaning structure comprises a fixing base (1) connected to the cleaner body and a number of brush heads (2) arranged on the fixing base (1). The brush heads (2) are made of silica gel, and are of a hexagon shape and a hollow structure. The number of brush heads (2) are arranged on the fixing base (1) in an array and distributed in a cellular arrangement. By arranging the cellular brush heads (2) of a hollow structure and utilizing a suction force produced by the tightly-attached brush heads (2) during use, dirt on the skin surface is sucked automatically by means of a sucking disc principle in a process of contact with the skin, to allow more thorough cleaning.

Despite the foregoing developments, there is still room in the art for further improvement.

All references cited herein are incorporated herein by reference in their entireties.

BRIEF SUMMARY OF THE INVENTION

Accordingly, the invention comprises a device and a method for treating dermatitis, psoriasis, acne and other disorders of the skin, which address the problems of the prior art described above. Preferably, the invention comprises a skin treatment device that uses regulated positive pressure (compression), a releasable seal, and a greater amount of negative pressure (vacuum) in repeated movements to force water into and across the skin and then remove the water and debris from the treated area. Without wishing to be bound by theory, it is believed that the device both lavages the skin and extracts inflammatory exudates and cytokines as well as clears inflammatory debris and microabscesses, allowing the skin to heal and restore its natural properties. The end result is remission of the original inflammatory condition and suppression of the body's autoimmune response that underlies many skin disorders.

A first aspect of the invention is a skin treatment device comprising:
an enclosure configured to selectively admit and expel air and water, said enclosure comprising a distal end, a proximal end and a hollow center defining a chamber closed at the distal end and having an opening at the proximal end, wherein the enclosure has sufficient elasticity for repeated compression and decompression along a longitudinal axis thereof;
a lip provided around a perimeter of the opening at the proximal end of the enclosure, and having sufficient elasticity for repeated compression and decompression;
protrusions and channels on a proximal surface of the lip, wherein the protrusions and channels have sufficient elasticity for repeated compression and decompression and are configured to selectively: (i) permit a flow of air and water to be expelled from the chamber of the enclosure through the channels as the skin treatment device is initially compressed against the skin; (ii) terminate the flow of air and water from the chamber when the lip, protrusions and channels have been sufficiently compressed against the skin to form a seal between the lip and the skin; and (iii) permit air to enter the chamber through the channels when the seal is broken by decompression of the lip, protrusions and channels upon decompression of the device; and
at least one outlet valve on the enclosure which is configured to permit an additional flow of air and water out of the chamber to regulate pressure as the enclosure is being compressed against the skin, and to resist admission of air or water into the chamber as the enclosure is being decompressed.

In certain embodiments, the channels comprise external perimeter walls and internal perimeter walls, which have a height less than a height of the protrusions such that upon compression of the protrusions against the skin, the external perimeter walls and the internal perimeter walls are configured to contact the skin to seal the channels and provide a plurality of sealed compartments around the lip, and wherein the sealed compartments are configured to apply suction to the skin as the device is decompressed and increase an amount of decompression force required to remove the device from the skin.

In certain embodiments, the skin treatment device further comprises: (a) a strap on the distal end of the enclosure and configured to receive and removably retain at least a portion of a hand of a user of the skin treatment device; or (b) a handle shaped and sized to be gripped by a human hand and extending distally from the distal end of the enclosure.

In certain embodiments that include the strap, the strap is configured to receive at least one finger of the user and possesses elasticity.

In certain embodiments, the enclosure and the lip comprise a material independently selected from the group consisting of silicone, silicone rubber, rubber, neoprene, polyurethane, nitrile rubber, butyl rubber, chlorosulfonated polyethylene, ethylene propylene diene monomer, styrene-butadiene rubber, ethylene propylene diene monomer, chloroprene rubber, fluoroelastomer, acrylonitrile butadiene rubber, polybutadiene rubber, polyisoprene rubber, styrene-isoprene-styrene block copolymer, and styrene-butadiene-styrene block copolymer.

In certain embodiments, the lip is more flexible than the enclosure, has a convex circumferential wall with a smooth external surface and tapers inwardly in a proximal direction such that the smooth external surface is configured to contact the skin as the skin treatment device is compressed so as to form an outermost circumference of the seal formed between the lip and the skin as the protrusions and the channels of the proximal surface of the lip are fully compressed against the skin.

In certain embodiments, the skin treatment device further comprises at least one spring housed within the enclosure and configured to provide resistance against the device being compressed against the skin.

In certain embodiments, the at least one spring is a helical spring configured to be compressed to its solid height by applying a force within a range from 0.44 N to 44 N.

In certain embodiments, the enclosure is sufficiently resilient to provide a spring-like effect and the skin treatment device is free of a separate spring.

In certain embodiments, the at least one outlet valve comprises a resealable slit through the enclosure.

In certain embodiments, the enclosure and the lip have a circular, elliptical or kidney-shaped transverse cross-section.

In certain embodiments, the channels fully extended radially across the proximal surface of the lip.

In certain embodiments, the skin treatment device further comprises a motor, a control button and control electronics configured to repeatedly compress and decompress the enclosure to repeatedly form and break the seal between the lip and the skin.

In certain embodiments, the protrusions are configured to expand to initiate breaking of the seal upon the decompression of the device.

In certain embodiments, the skin treatment device is sufficiently flexible to conform to contours and crevices of the skin.

A second aspect of the invention is a method for treating a skin disorder, said method comprising the following steps:
(a) providing the skin treatment device of the invention;
(b) providing a volume of water in the chamber;
(c) placing the lip in contact with the skin;
(d) compressing the enclosure against the skin by applying an amount of compression force so as to apply the water in the chamber to the skin;
(e) terminating the compressing when the seal between the lip and the skin is formed, to provide an internal air pressure in the chamber of the device less than an ambient air pressure outside the device;
(f) pulling the enclosure away from the skin to decompress the enclosure, generate suction to draw water and debris away from the skin, decompress the protrusions, channels and lip to break the seal between the lip and the skin, and remove the enclosure from the skin;
(g) allowing at least some of the volume of water remaining in the chamber to drain out; and
(h) repeating steps (b) through (g) at least once.

In certain embodiments, step (h) is repeated 9-15 times for each area of skin to be treated.

In certain embodiments, the skin disorder is psoriasis, dermatitis, acne or eczema.

In certain embodiments, the volume of water in each iteration of step (b) is 1-250 ml, a temperature of the water is 36.7° C. to 41.1° C., and cycles consisting of steps (b) through (g) are conducted at a rate of 30-180 cycles per minute.

In certain embodiments, the amount of the compression force applied in step (d) of each of the cycles is from 0.44 N to 44 N.

In certain embodiments, an amount of a decompression force applied in step (f) of each of the cycles is from −0.45 N to −45 N, and is greater than the amount of compression force applied in step (d).

In certain embodiments, the method is conducted free of medicaments and free of cleansing agents other than water.

In certain embodiments, the method further comprises applying a moisturizer to the skin as a final step.

In certain embodiments of the method, the protrusions expand to initiate the breaking of the seal upon the decompression of the device.

In certain embodiments of the method, the device flexibly conforms to contours and crevices of the skin in the compressing step.

A third aspect of the invention is a skin treatment device for treating skin comprising:
an enclosure configured to selectively admit and expel air and water, said enclosure comprising a distal end, a proximal end and a hollow center defining a chamber closed at the distal end and having an opening at the proximal end, wherein the enclosure has sufficient elasticity for repeated compression and decompression along a longitudinal axis thereof;
a lip provided around a perimeter of the opening at the proximal end of the enclosure, and having sufficient elasticity for repeated compression and decompression;
at least one outlet valve on the enclosure which is configured to selectively: (i) permit a flow of air and water to be expelled from the chamber of the enclosure through the at least one outlet valve as the skin treatment device is initially compressed against the skin; (ii) terminate the flow of air and water from the chamber when the lip has been sufficiently compressed against the skin to form a seal between the lip and the skin; and (iii) resist admission of air or water into the chamber as the enclosure is being decompressed; and
at least one inlet valve configured to permit air to enter the chamber during decompression to break the seal between the lip and the skin.

In certain embodiments, the at least one outlet valve and the at least one inlet valve are the same two-way valve.

A fourth aspect of the invention is a method for treating a skin disorder, said method comprising the following steps:
(a) providing the skin treatment device of the third aspect of the invention;
(b) providing a volume of water in the chamber;
(c) placing the lip in contact with the skin;
(d) compressing the enclosure against the skin by applying an amount of compression force so as to apply the water in the chamber to the skin;
(e) terminating the compressing when the seal between the lip and the skin is formed, to provide an internal air pressure in the chamber of the device less than an ambient air pressure outside the device;
(f) pulling the enclosure away from the skin to decompress the enclosure, generate suction to draw water and debris away from the skin, and remove the enclosure from the skin;
(g) allowing at least some of the volume of water remaining in the chamber to drain out; and
(h) repeating steps (b) through (g) at least once.

BRIEF DESCRIPTION OF SEVERAL VIEWS OF THE DRAWINGS

The patent or application file contains at least one drawing executed in color. Copies of this patent or patent application publication with color drawing(s) will be provided by the Office upon request and payment of the necessary fee.

The invention will be described in conjunction with the following drawings. The components in the drawings are not necessarily to scale, emphasis instead being placed upon clearly illustrating the principles of the present disclosure. Moreover, in the drawings, like reference numerals designate like elements, wherein:

FIG. 7A is a pre-treatment photograph of the foot of Subject 2 of Example 2.

FIG. 7B is a photograph of the foot of Subject 2 after one week of treatment.

FIG. 7C is a photograph of the foot of Subject 2 after three weeks of treatment.

FIG. 8A is a pre-treatment photograph of the forehead of Subject 3 of Example 3.

FIG. 8B is a photograph of the forehead of Subject 3 after one week of treatment.

FIGS. 13B and 13C are close-up photographs of the eczema lesions shown in FIG. 13A.

FIGS. 13D and 13E are post-treatment photographs corresponding to the pre-treatment photographs of FIGS. 13B and 13C.

DETAILED DESCRIPTION OF PREFERRED EMBODIMENTS OF THE INVENTION

Figure 1A:
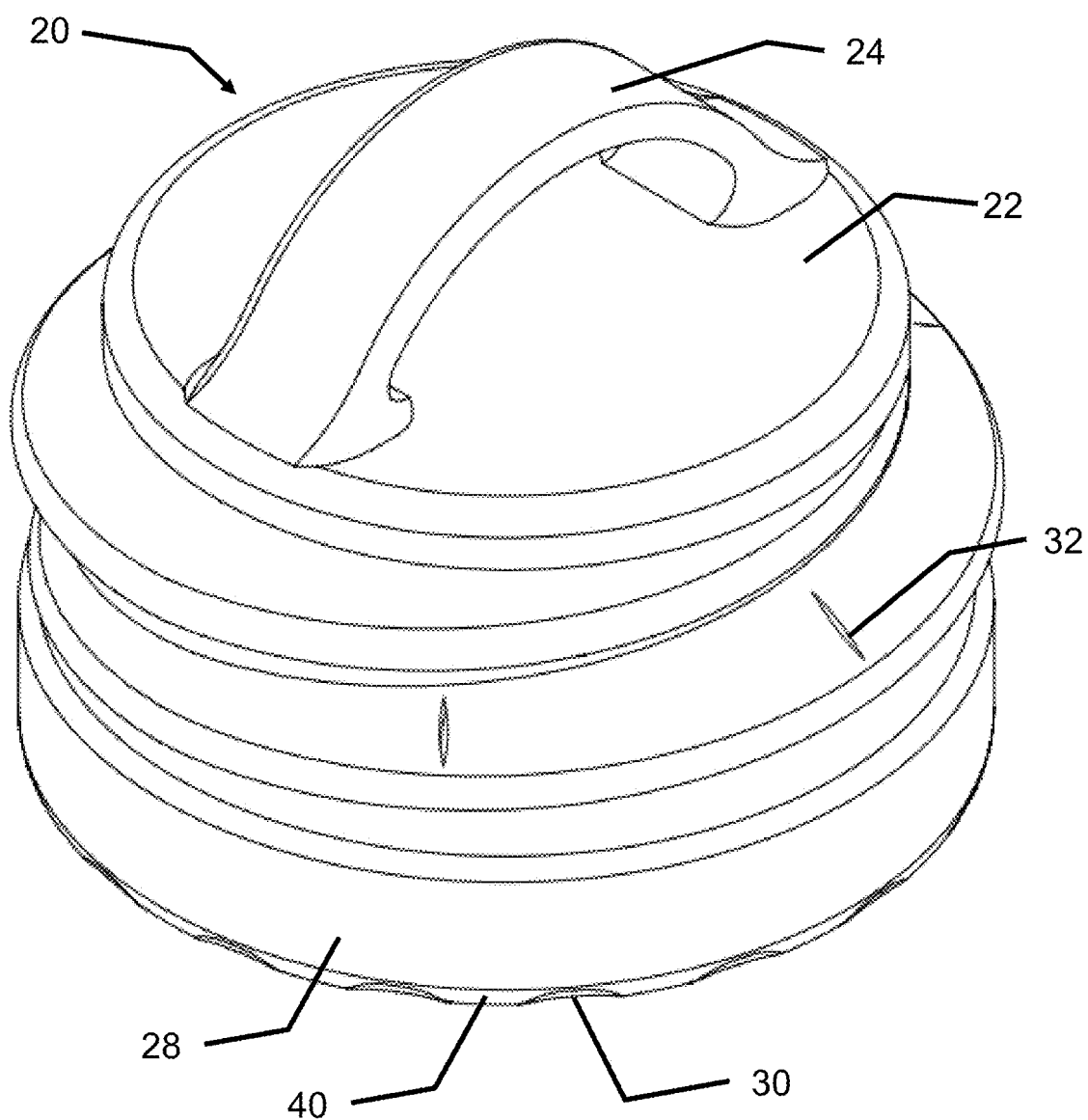
FIG. 1A is a front isometric view of a first embodiment of a skin treatment device of the invention.
Figure 1B:
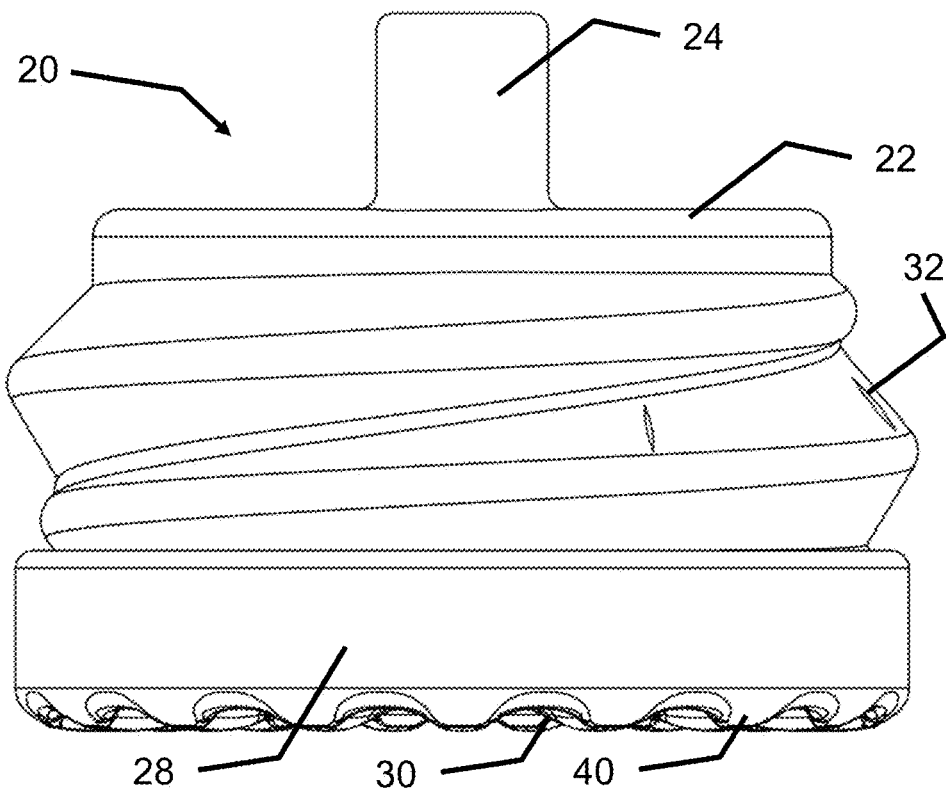
FIG. 1B is a front view of the skin treatment device shown in FIG. 1A.

The method and apparatus of the invention are based in part on the surprising discovery by the inventor that the application of water to the skin under varied pressure alternated with intervals of varied suction alleviates the symptoms (e.g., inflammation) of skin disorders, such as dermatitis and psoriasis, and preferably causes the disorder to be in remission. Unlike the prior art, the method and apparatus of the invention do not require medicaments or cleansing agents (other than water alone, to the extent it is deemed a cleansing agent), and do not suffer from associated side effects thereof.

Skin Treatment Device

Referring to FIGS. 1A-1K, 2A-2I, 3A, 3B, 4A, 4B, 5A, 5B, 14A and 14B, device 20 comprises enclosure 22 having a distal end, a proximal end and a hollow center defining chamber 36 closed at the distal end and having opening 26 at the proximal end. Enclosure 22 has sufficient elasticity for repeated compression and decompression along a longitudinal axis thereof (i.e., an axis running from proximal end to distal end).

In addition to being elastic, enclosure 22 is a structure capable of selectively retaining water. It can be completely or partially water-tight when held against the skin 48 being treated.

Lip 28 is provided around a perimeter of opening 26 at the proximal end. A plurality of channels 30 extend radially across lip 28 between protrusions 40 so as to selectively permit air and a portion of water applied to the skin with skin treatment device 20 to escape from chamber 36 as enclosure 22 is compressed against the skin to form a seal, which is preferably a vacuum seal, which as defined herein is a closure sufficiently airtight to maintain air pressure within the chamber lower than ambient air pressure outside the chamber. Channels 30 also allow air to flow into chamber 36 during decompression of enclosure 22 and lip 28 as device 20 moves away from skin and to facilitate release of device 20 from the skin.

FIGS. 1H, 1I, 1J and 1K are a sequence of drawings showing the conformational changes of device 20 as it is compressed against skin 48. As device 20 is compressed against skin 48, protrusions 40 and channels 30 are progressively compressed until internal perimeter walls 44 and external perimeter walls 42 contact skin 48, substantially sealing each channel 30, to form multiple sealed compartments around lip 28. The air pressure within the compartments is lower than the ambient pressure outside device 20. It is also within the scope of the invention to form the sealed compartments in less than all of the channels, and/or to have at least some channels without internal perimeter walls 44 and/or without external perimeter walls 42.

Enclosure 22 further comprises four outlet valves 32 spaced apart about the perimeter thereof, which are configured to permit a flow of air and water out of chamber 36 to modulate pressure when enclosure 22 is being compressed against the skin, and to resist a flow of air and/or water into chamber 36 to enhance suction against the skin when enclosure 22 is being decompressed. In alternative embodiments, the number of outlet valves may be less than 4 (i.e., 1, 2 or 3) or greater than 4 (e.g., 5, 6, 7, 8, 9 or 10).

In certain embodiments, outlet valves 32 are preferably covered over and closed by the walls of enclosure 22, which overlap outlet valves as device 20 is compressed, facilitating the seal being formed between the device and the skin.

Open outlet valves 32 and non-compressed protrusions 40 allow for the maximum force of water to be applied to and across skin 48 upon initial compression of device 20. Upon further compression of device 20, closed outlet valves 32, compressed protrusions 40, compressed channels 30 and the inwardly rolling circumferential wall 46 of lip seal device 20 to the skin. Upon decompression of device 20, the at least one protrusion 40 expands back to its original (i.e., non-compressed or fully decompressed) shape to facilitate breaking of the seal to allow air to enter chamber 36, and a sudden popping sound may be evident as the seal of lip 28 to skin 48 is released, resulting in water and undesirable materials being drawn away from skin 48 by suction.

Figure 4A:
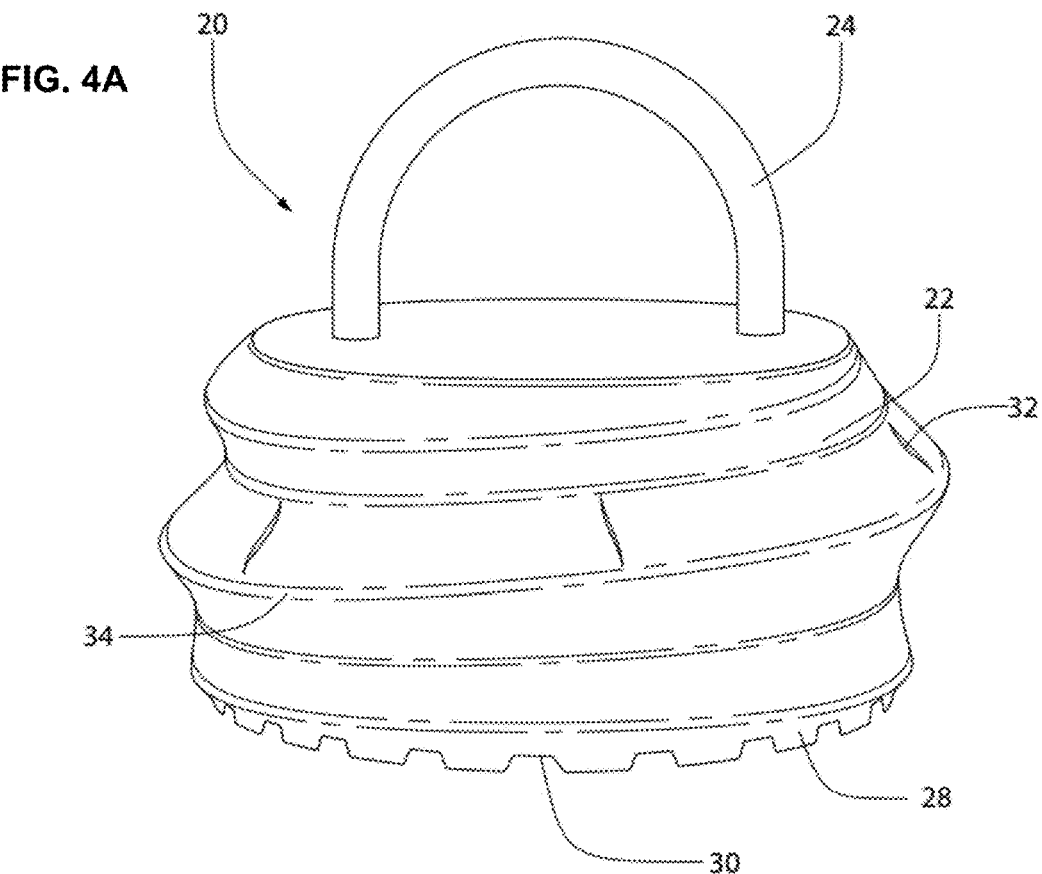
FIG. 4A is a front perspective view of an eighth embodiment of a skin treatment device of the invention.
Figure 4B:
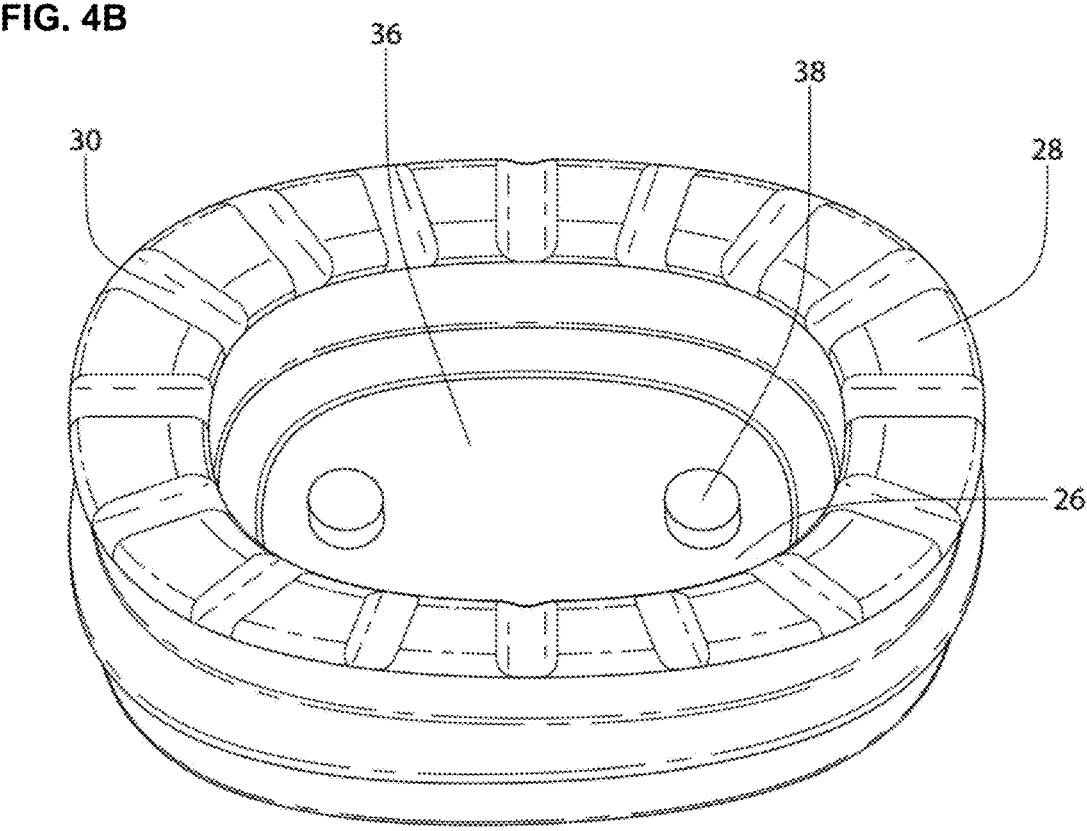
FIG. 4B is a bottom perspective view of the skin treatment device shown in FIG. 4A.
Figure 5A:
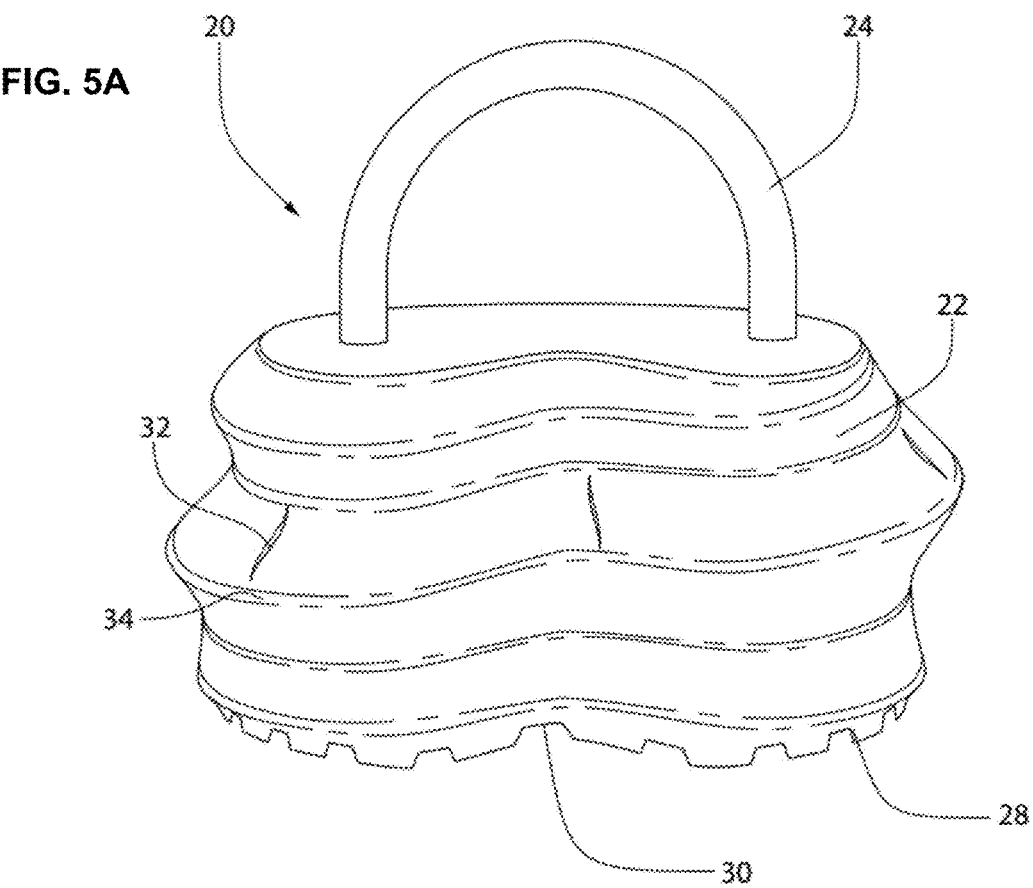
FIG. 5A is a front perspective view of a ninth embodiment of a skin treatment device of the invention.
Figure 5B:
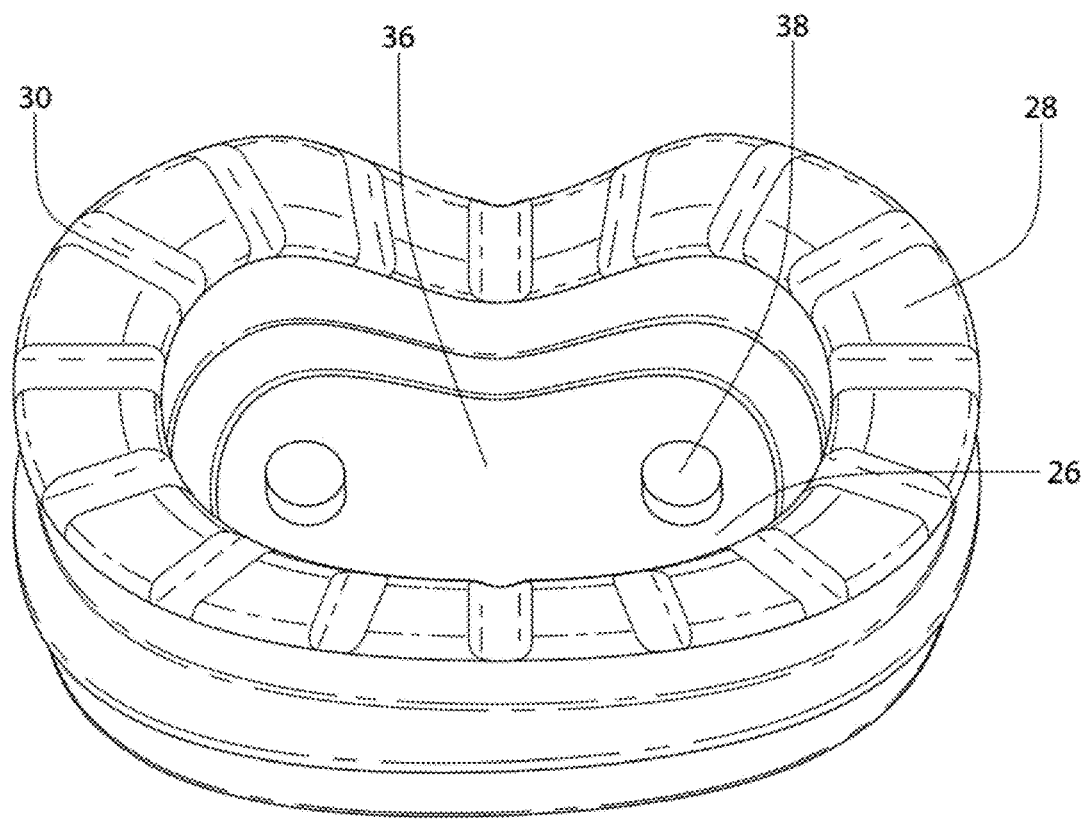
FIG. 5B is a bottom perspective view of the skin treatment device shown in FIG. 5A.

Device 20 preferably comprises strap 24 to better secure device 20 to user's hand. In the embodiments of FIGS. 3A, 3B, 4A, 4B, 5A and 5B, strap 24 is simply an elastic cord which passes through the distal end of enclosure 22 to form a loop for receiving at least one finger of the user. Strap 24 has anchors 38 at each end thereof which prevent the ends from passing through the distal end of enclosure 22. FIGS. 3B, 4B and 5B show anchors 38 as cylinders having diameters greater than the those of strap 24 and the holes (not shown) in the distal end of enclosure 22 through which strap 24 passes. In certain alternative embodiments, anchors 38 are, e.g., knotted ends of strap 24, or any other structure on each end of strap 24 whose dimensions prevent the removal of strap 24 from device 20.

In alternative embodiments, the strap can be, e.g., unitarily formed from the same material as the enclosure, which material is preferably resilient. See, e.g., FIGS. 1A-1K and 2A-2I, in which strap 24 is unitarily formed with enclosure 22 by, e.g., injection molding, compression molding, transfer molding, extrusion, 3-D printing, or other means. Thus, there are no anchors in these embodiments.

Figure 1C:
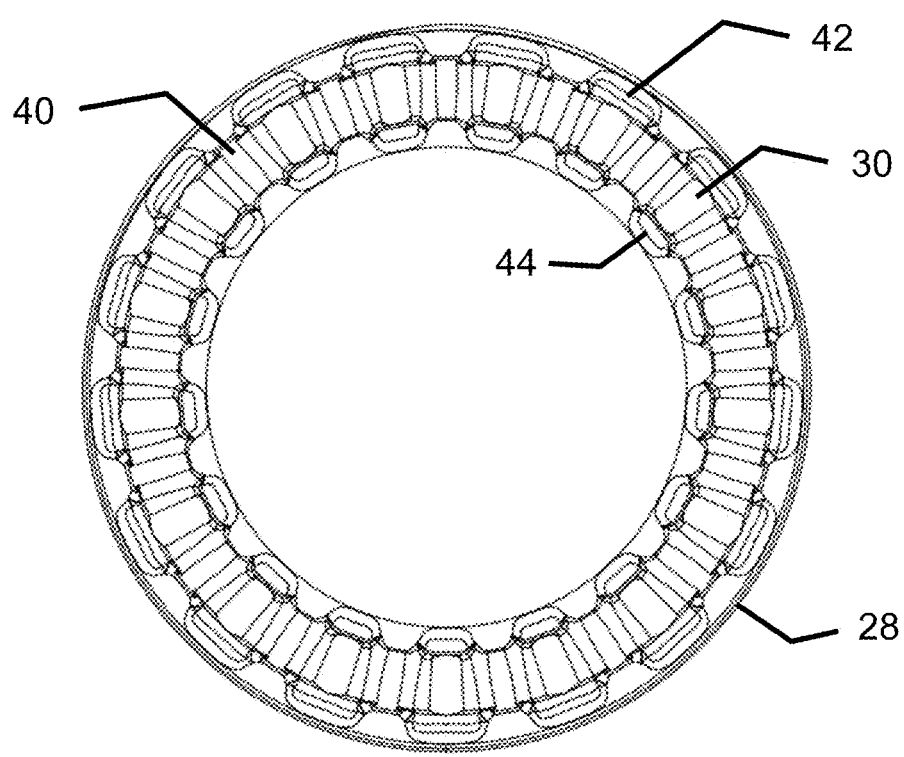
FIG. 1C is a bottom view of the skin treatment device shown in FIG. 1A.
Figure 1D:
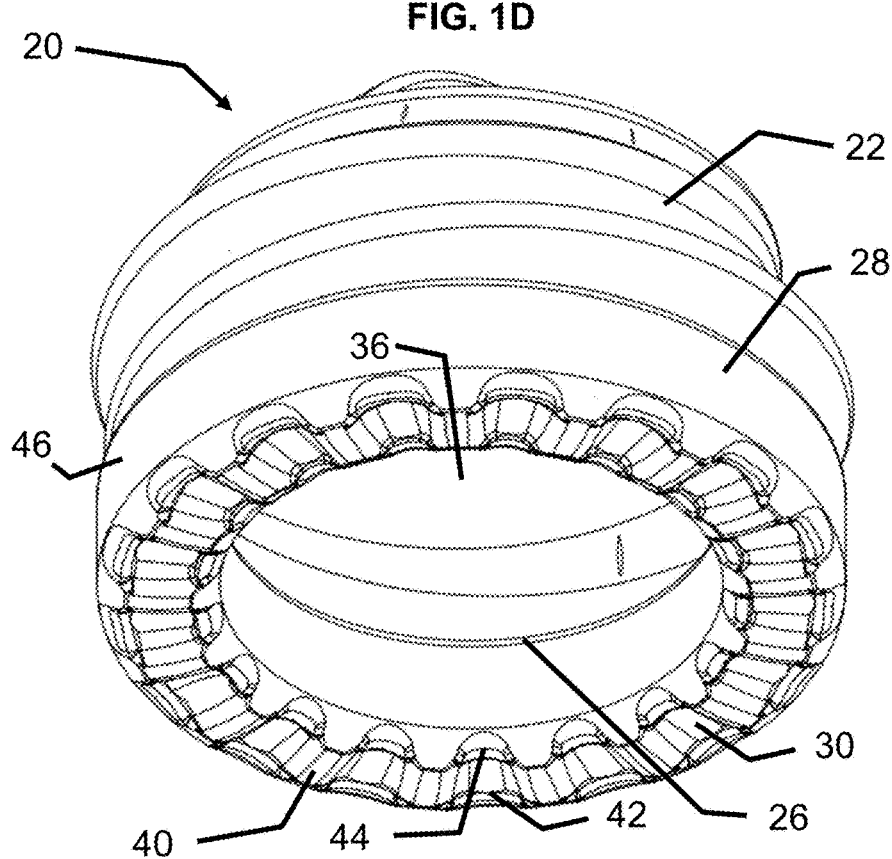
FIG. 1D is a back bottom isometric view of the skin treatment device shown in FIG. 1A.
Figure 1E:
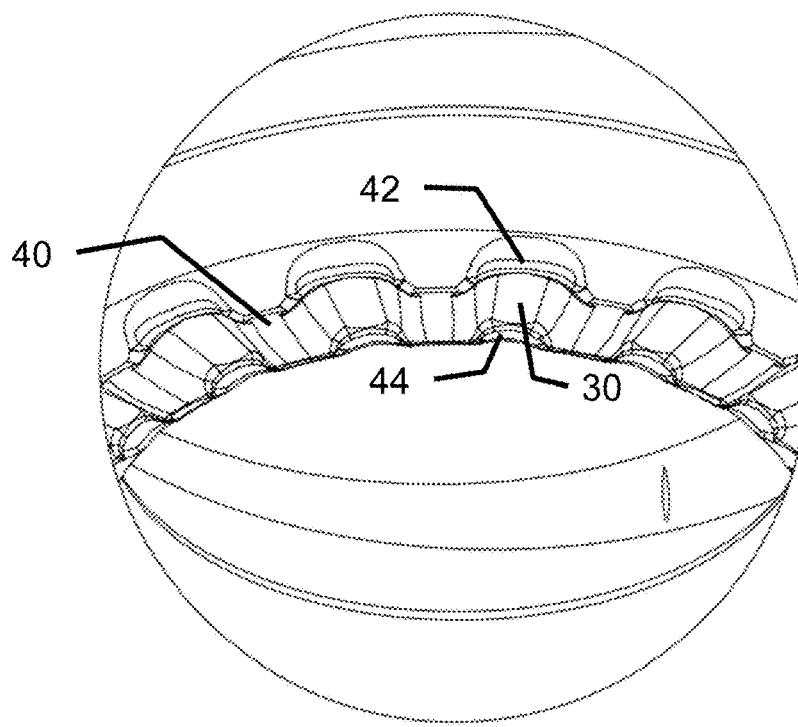
FIG. 1E is a magnified view of a portion of FIG. 1D.
Figure 1F:
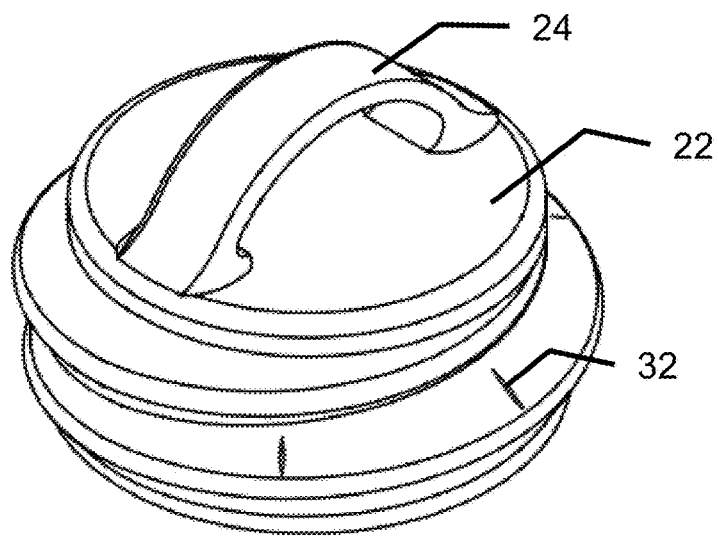
FIG. 1F is an exploded view of the skin treatment device shown in FIG. 1A.
Figure 1F:
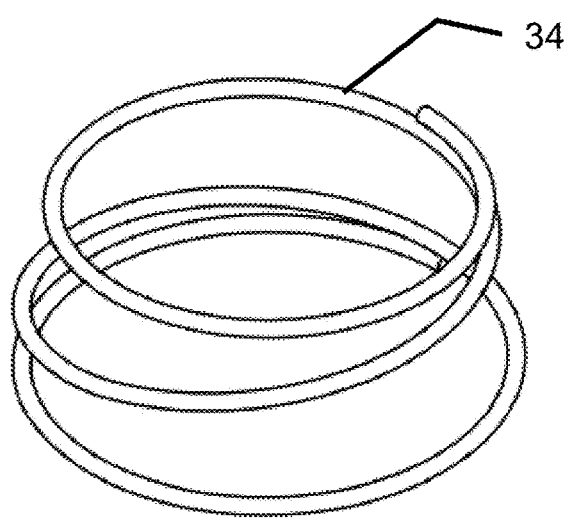
Figure 1F:
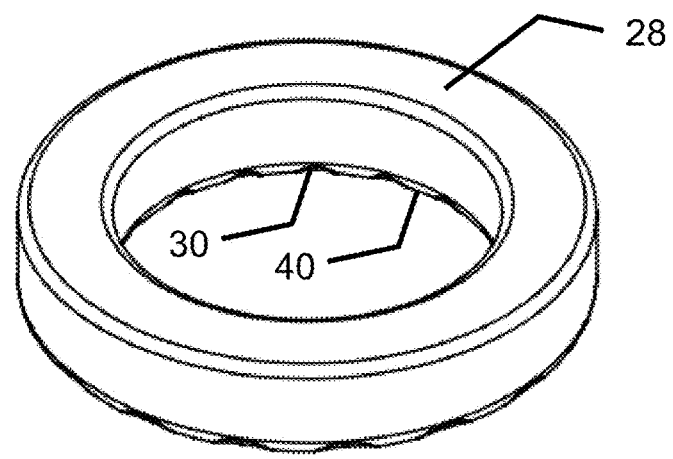
Figure 1G:
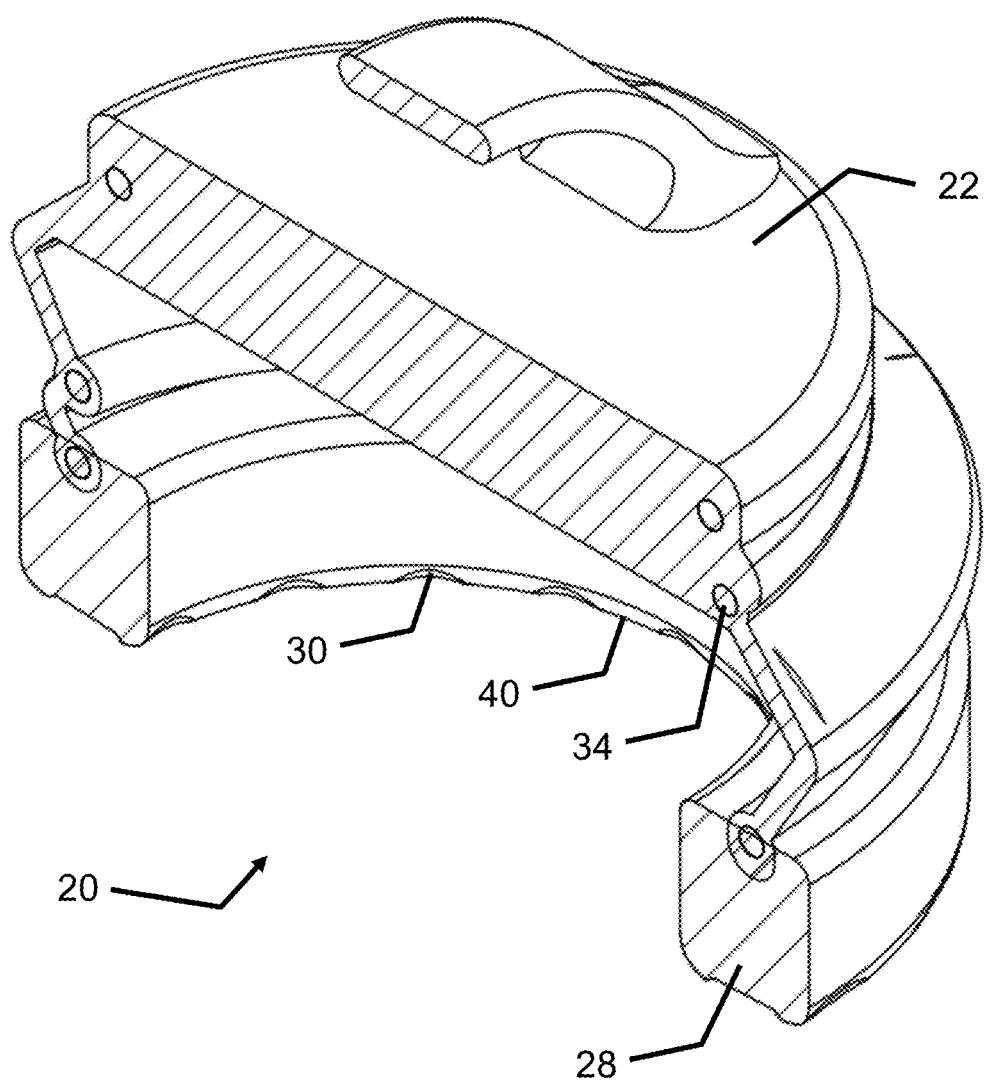
FIG. 1G is an isometric section view of the skin treatment device shown in FIG. 1A.
Figure 1H:
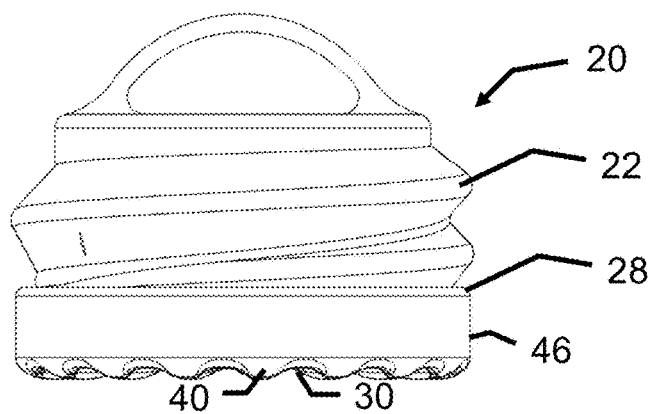
FIG. 1H is a side view of the skin treatment device shown in FIG. 1A in an uncompressed state.
Figure 1I:
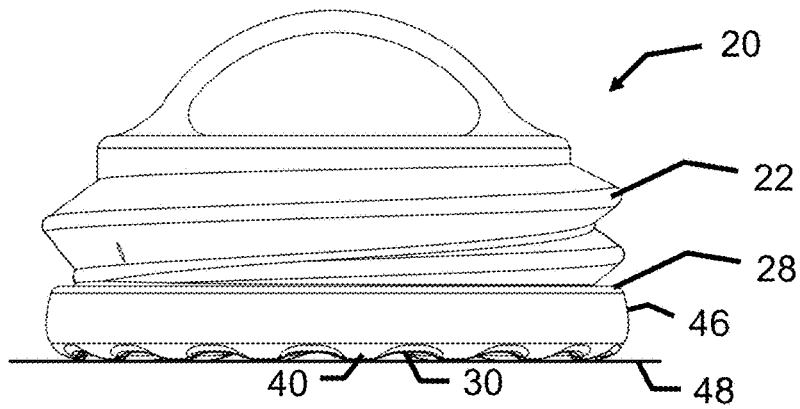
FIG. 1I is a side view of the skin treatment device shown in FIG. 1A in a partially compressed state.
Figure 1J:
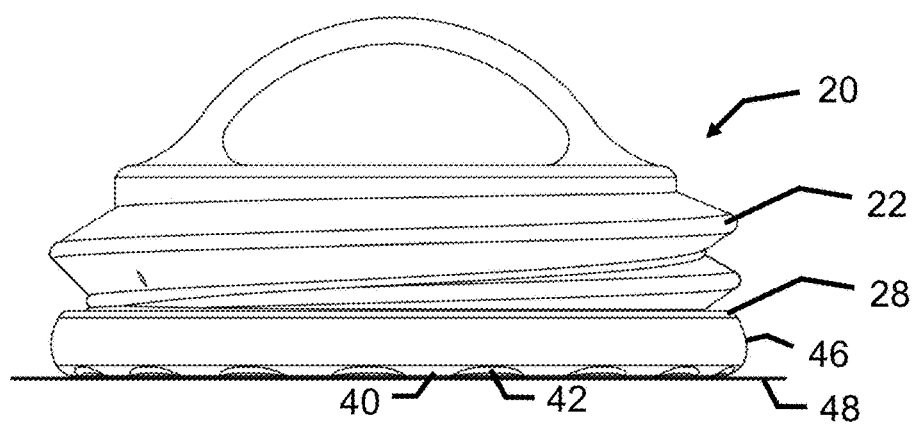
FIG. 1J is a side view of the skin treatment device shown in FIG. 1A in a further compressed state.
Figure 1K:
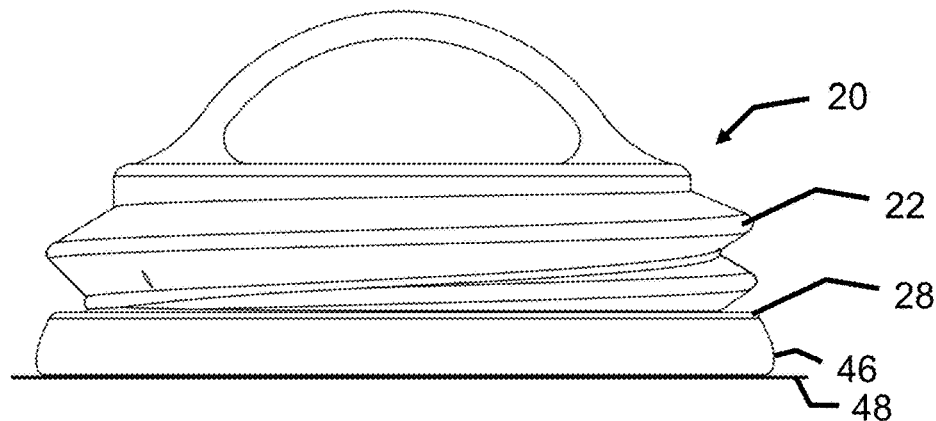
FIG. 1K is a side view of the skin treatment device shown in FIG. 1A in a fully compressed state.
Figure 1L:
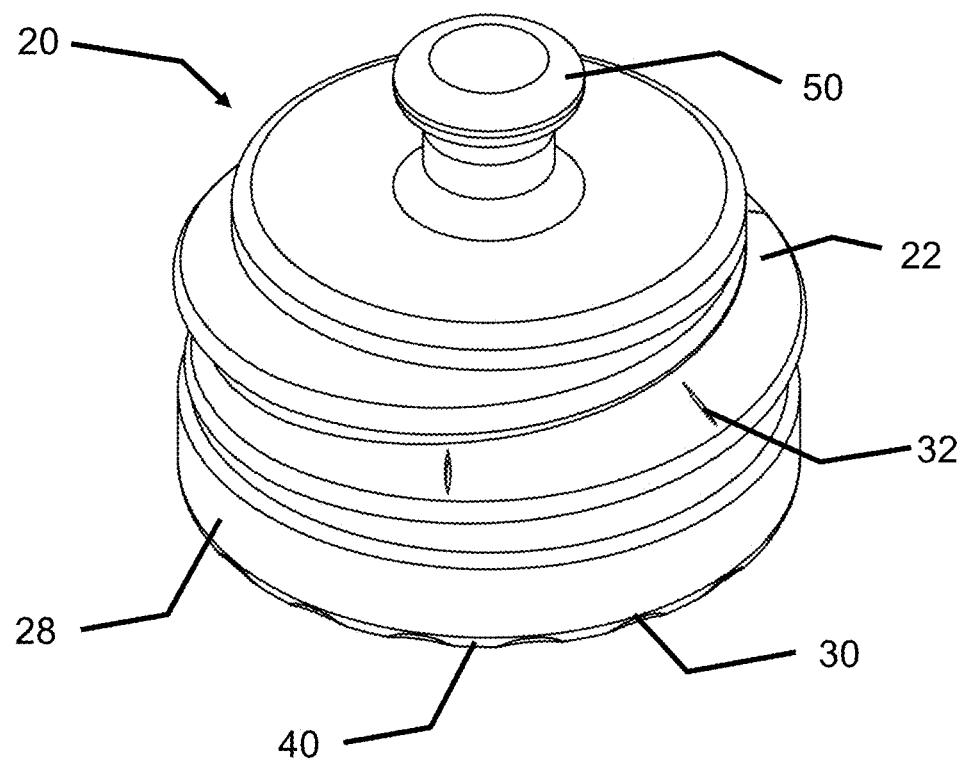
FIG. 1L is a front isometric view of a second embodiment of a skin treatment device of the invention, which is identical to the first embodiment except that the strap is replaced with a handle.

In still further alternative embodiments, device 20 has a handle 50 instead of a strap (see FIG. 1L). Handle 50 is preferably an elongated structure extending distally from the distal end of enclosure 22, which is shaped and sized to be gripped by a human hand in whole or in part. Handle 50 preferably has a contoured surface designed to fit comfortably within the user's hand or between the user's fingers, and/or a textured grip to prevent slipping during use. In certain embodiments, enclosure 22 and handle 50 are constructed from the same material, and are preferably unitarily formed from said material. In other embodiments, handle 50 is constructed of a less elastic material or materials than the other components of device 20, such as, e.g., polypropylene, polyethylene, polycarbonate, acrylonitrile butadiene styrene), wood, metal, rubber or silicone.

Figure 1M:
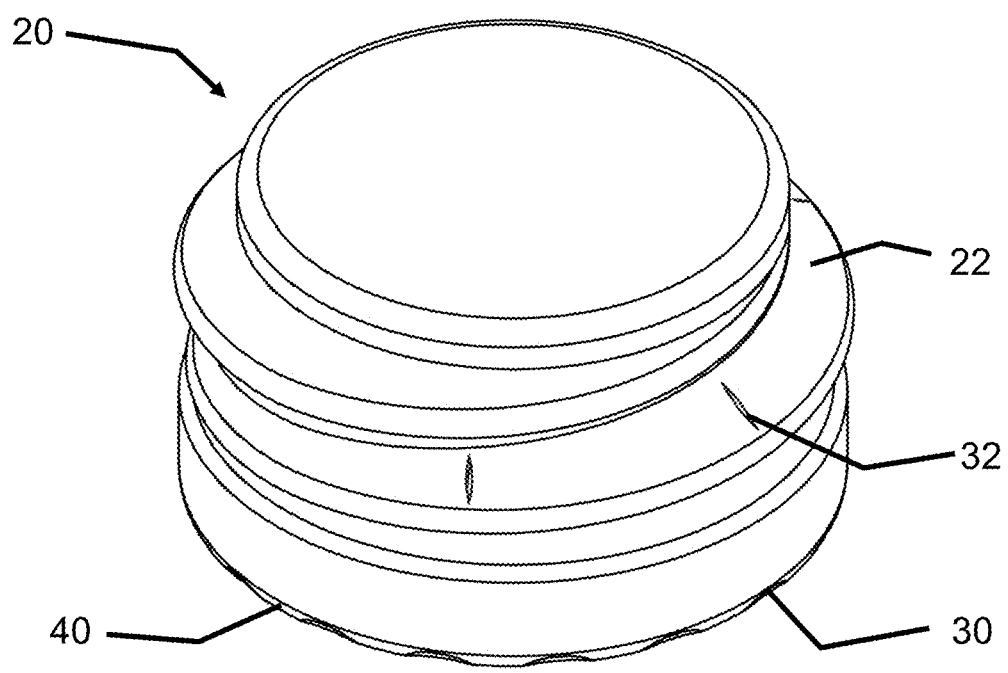
FIG. 1M is a front isometric view of a third embodiment of a skin treatment device of the invention, which is identical to the first and second embodiment except that there is no strap or handle.

It is also within the scope of the invention for device to have neither a strap nor a handle, as shown in FIG. 1M. In such embodiments, the user simply grips the sides of enclosure 22 to operate device 20. At least one textured surface (not shown) may optionally be provided on the sides of enclosure 22 to prevent slipping during use.

Embedded within the material of enclosure 22 is spring 34. See FIGS. 1F, 1G, 2G and 2H. Spring 34 is preferably a helical spring comprising an elastic material such as spring steel, which is preferably stainless steel. The performance properties of a spring depend on its geometry, stiffness, displacement to solid height, and resonant frequency. A spring can be used to regulate the depression force applied to compress the spring against an object, and then spring back when the depression force is released. The force required to compress a spring is proportional to the displacement of the spring. Therefore, the stiffness of the spring can be adjusted to regulate the depression force applied to the spring. The displacement to solid height is the distance the spring can be compressed before it reaches its solid height. The spring can be designed such that the displacement to solid height is equal to the depression force required to compress the spring against an object. When the depression force is released, the spring will return to its original position. In certain alternative embodiments, there is no separate spring, but rather, the materials of the enclosure are sufficiently resilient to provide the resistance to compression and the rebounding effect that would otherwise be provided by a spring.

In certain embodiments, enclosure 22, strap 24 and lip 28 are independently constructed from at least one elastomer and/or other elastic material. In certain other embodiments, two or more of enclosure 22, strap 24 and lip 28 are constructed from the same material, and are preferably unitarily formed from said material. Preferably, enclosure 22, strap 24 and lip 28 independently comprise at least one member selected from the group consisting of silicone, silicone rubber, rubber, neoprene, polyurethane, nitrile rubber, butyl rubber, chlorosulfonated polyethylene (e.g., HYPALON), VITON, ethylene propylene diene monomer, styrene-butadiene rubber, ethylene propylene diene monomer, chloroprene rubber, fluoroelastomer, acrylonitrile butadiene rubber, polybutadiene rubber, polyisoprene rubber, styrene-isoprene-styrene block copolymer, and styrene-butadiene-styrene block copolymer.

Flexibility of device 20 enables it to conform to various contours and crevices of the skin. Portions of device 20 may have different degrees of elasticity and/or be compressible to different degrees. Lip 28 is preferably more elastic than enclosure 22, but may also be of substantially the same elasticity. In certain embodiments, spring 34 within enclosure 22 provides enclosure with more rigidity than lip 28 even if, e.g., the materials from which spring 34 and enclosure 22 are constructed have the same elasticity.

Channels 30 are sized and shaped so as to permit at least a portion of water and air to flow out of chamber 36 upon initial compression of enclosure 22 and lip 28, and to permit air to flow into chamber 36 as enclosure 22 and lip are decompressed. Channels 30 and protrusions 40, between which channels 30 pass, have sufficient elasticity for repeated compression and decompression. The cross-sectional shapes of channels 30 are not particularly limited. Suitable channel shapes include but are not limited to cross-sectional shapes (viewed transverse to the radius of the lip) that are U-shaped, V-shaped or irregularly-shaped. Channels 30 preferably extend radially across lip 28, which engages with the skin of the person being treated. See, e.g., FIGS. 2B, 2C and 2F. In these figures, channels 30 are separated from each other by protrusions 40 provided on the proximal surface of lip 28. The protrusions and/or channels are non-limiting examples of surface irregularities, which as defined herein, are features that cause the surface of lip to be less than entirely smooth.

Figure 2A:
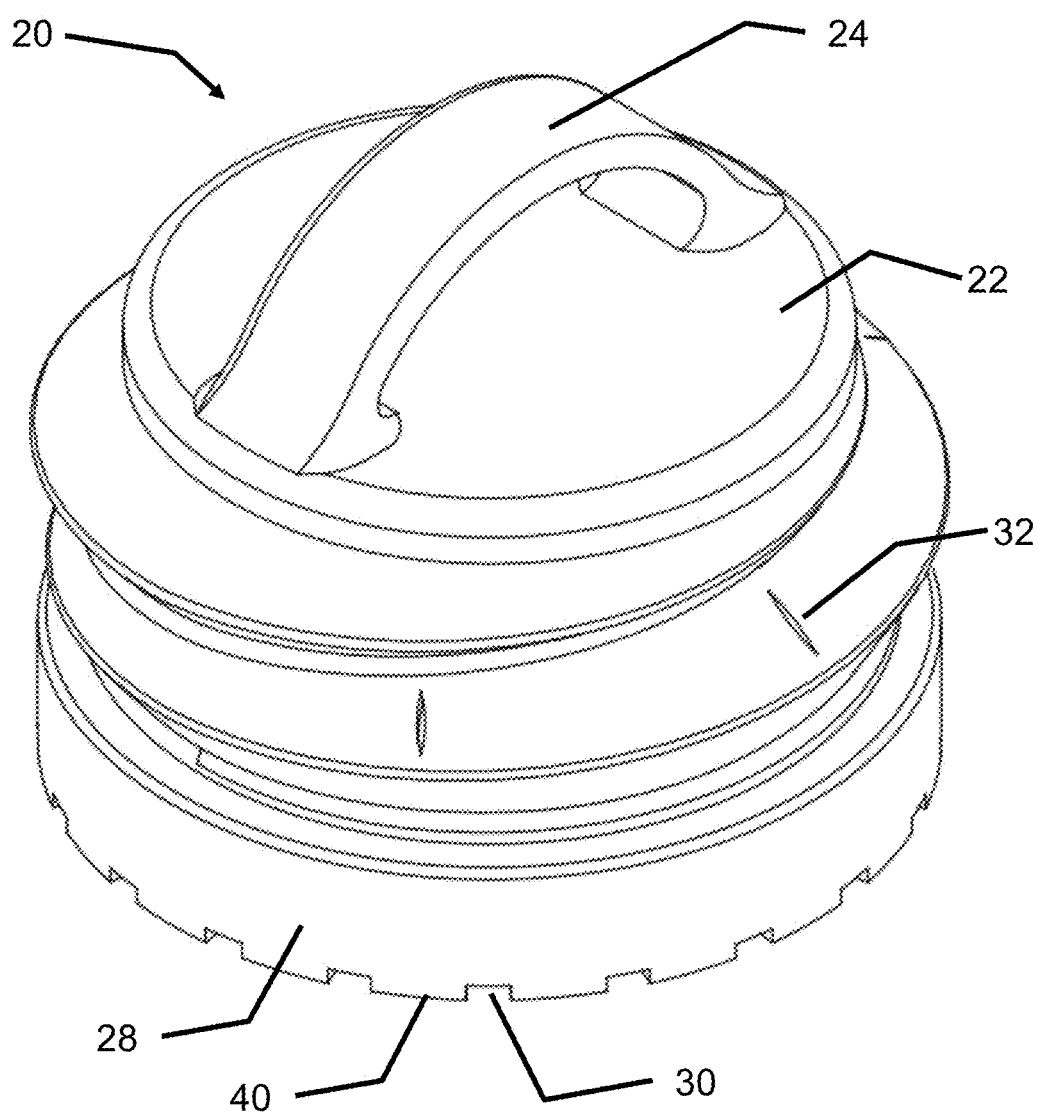
FIG. 2A is a front isometric view of a fourth embodiment of a skin treatment device of the invention.
Figure 2B:
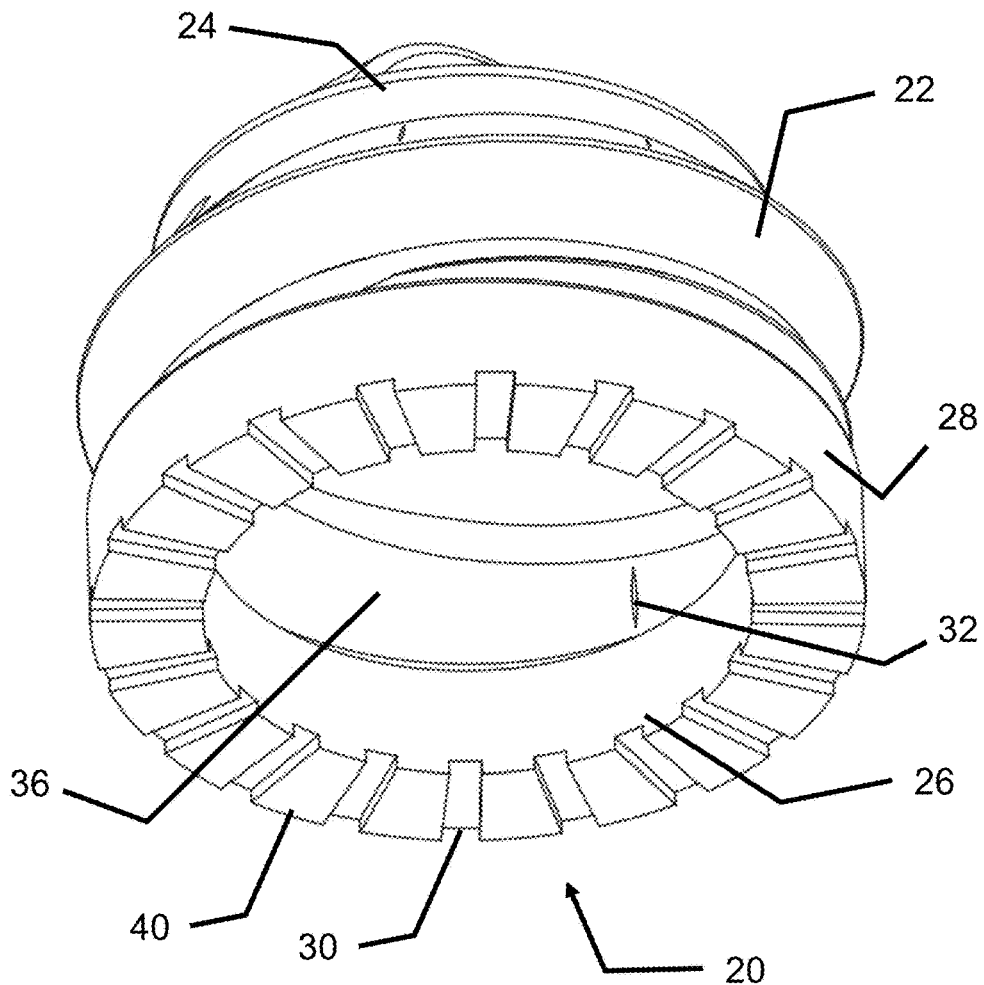
FIG. 2B is an isometric back bottom view of the skin treatment device of FIG. 2A.
Figure 2C:
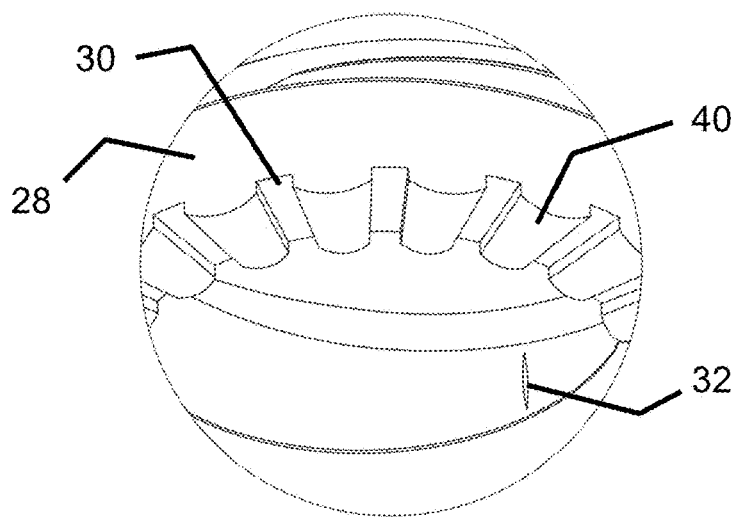
FIG. 2C is a magnified isometric back bottom view of the lip of a fifth embodiment of a skin treatment device of the invention.
Figure 2D:
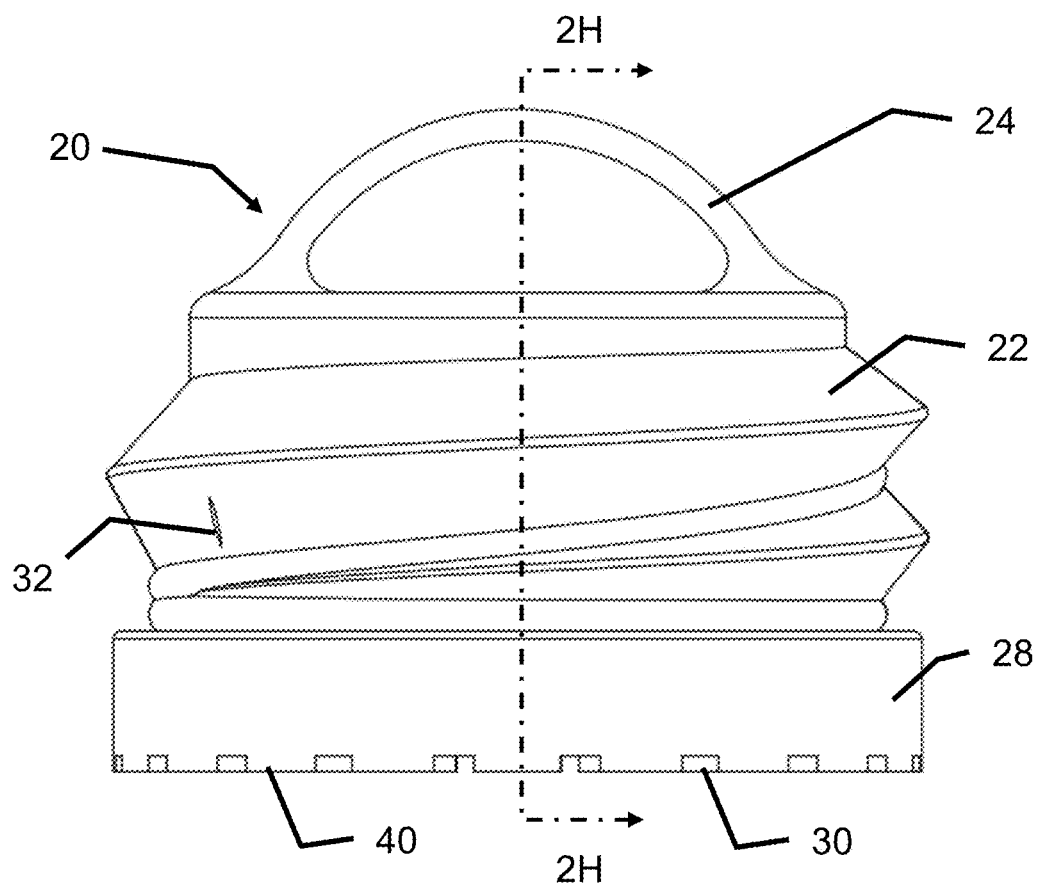
FIG. 2D is a side view of the skin treatment device of FIG. 2A.
Figure 2E:
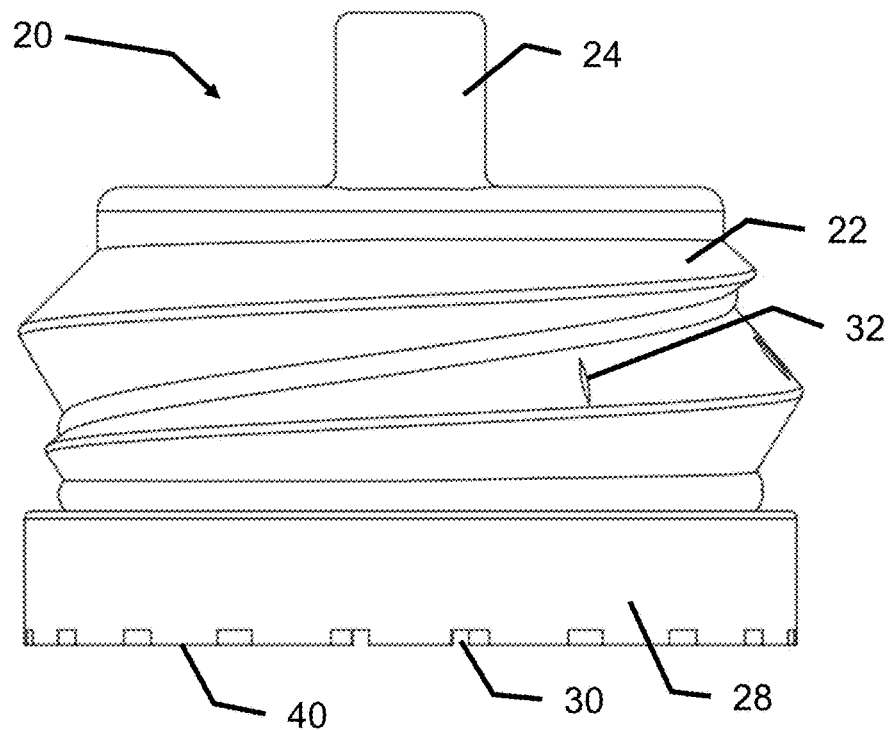
FIG. 2E is a front view of the skin treatment device of FIG. 2A.
Figure 2F:
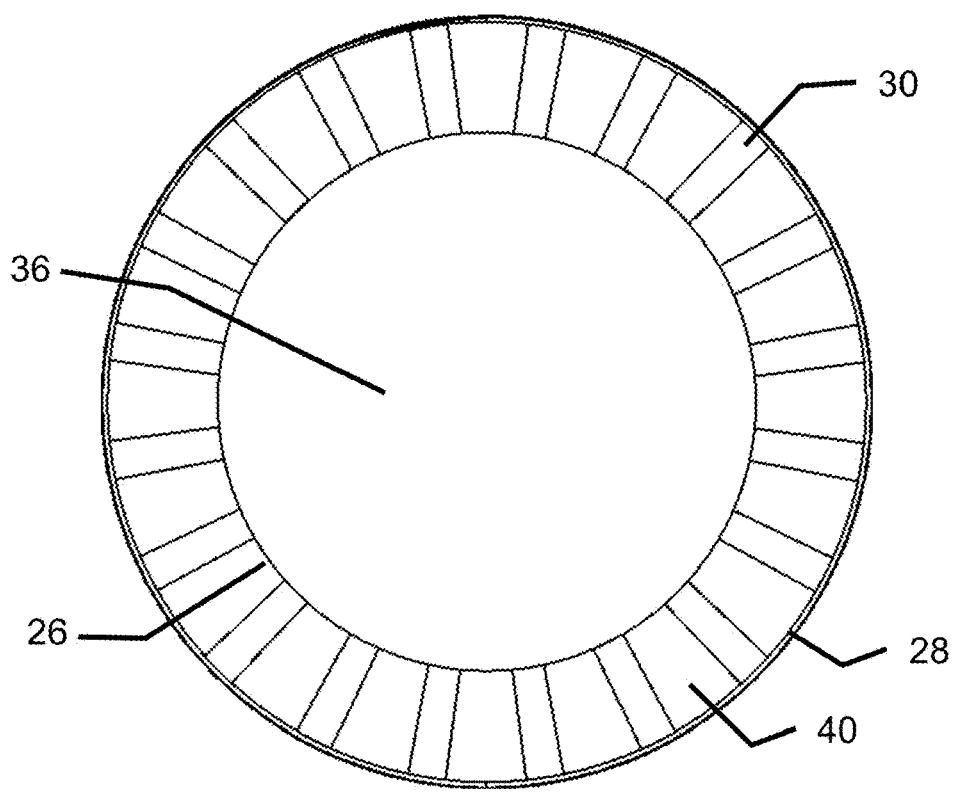
FIG. 2F is a bottom view of the lip of the skin treatment device of FIG. 2A.
Figure 2G:
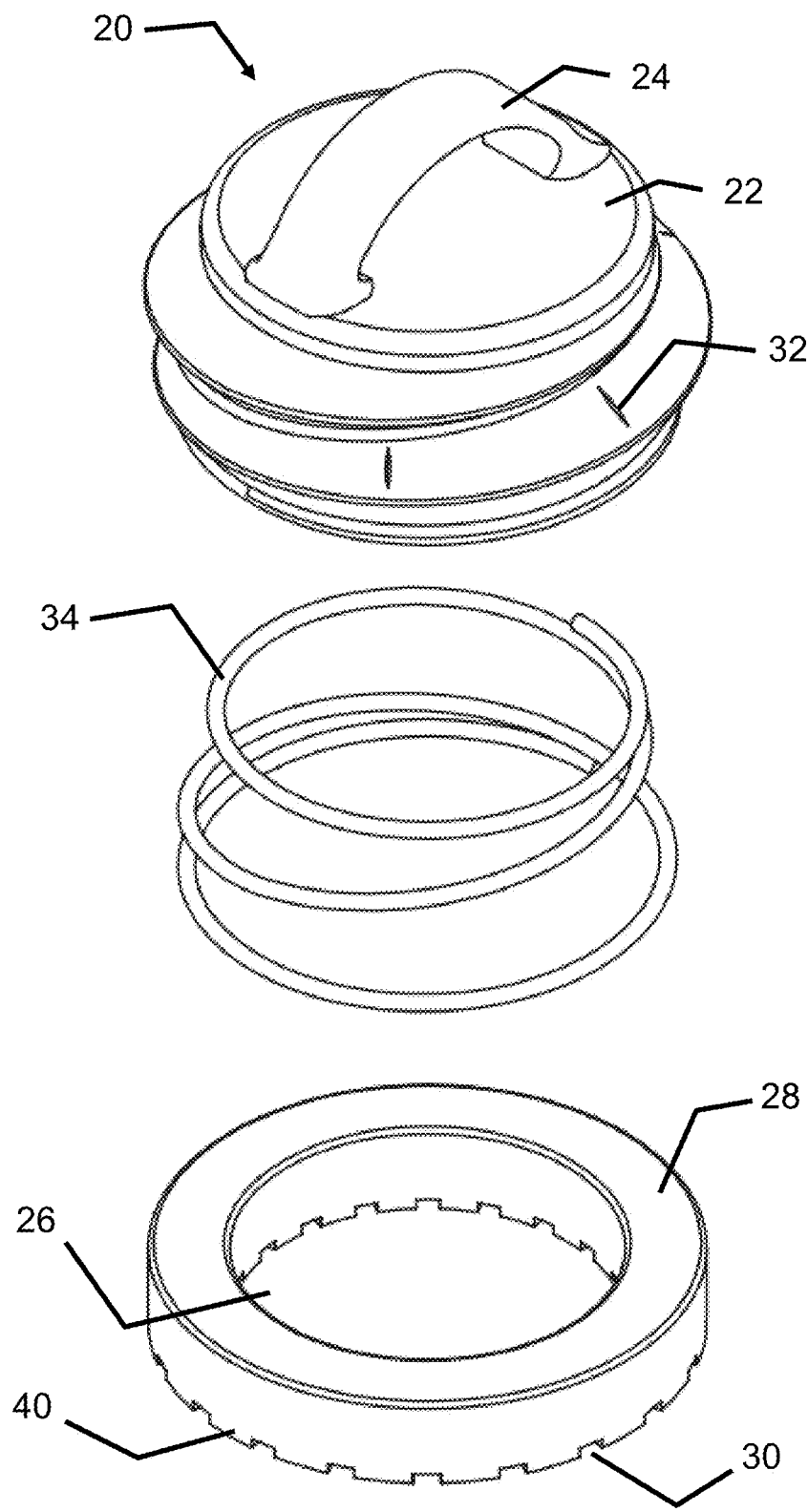
FIG. 2G is an exploded view of the skin treatment device of FIG. 2A.
Figure 2H:
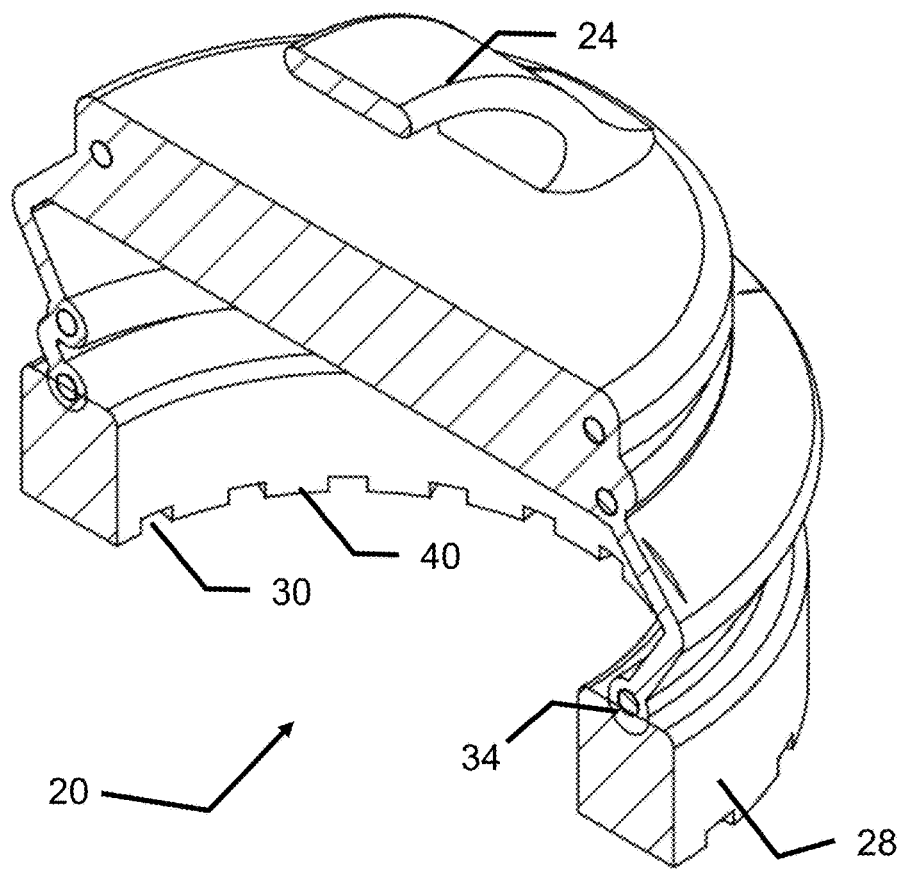
FIG. 2H is an isometric section view through line 2H-2H of FIG. 2D.
Figure 2I:
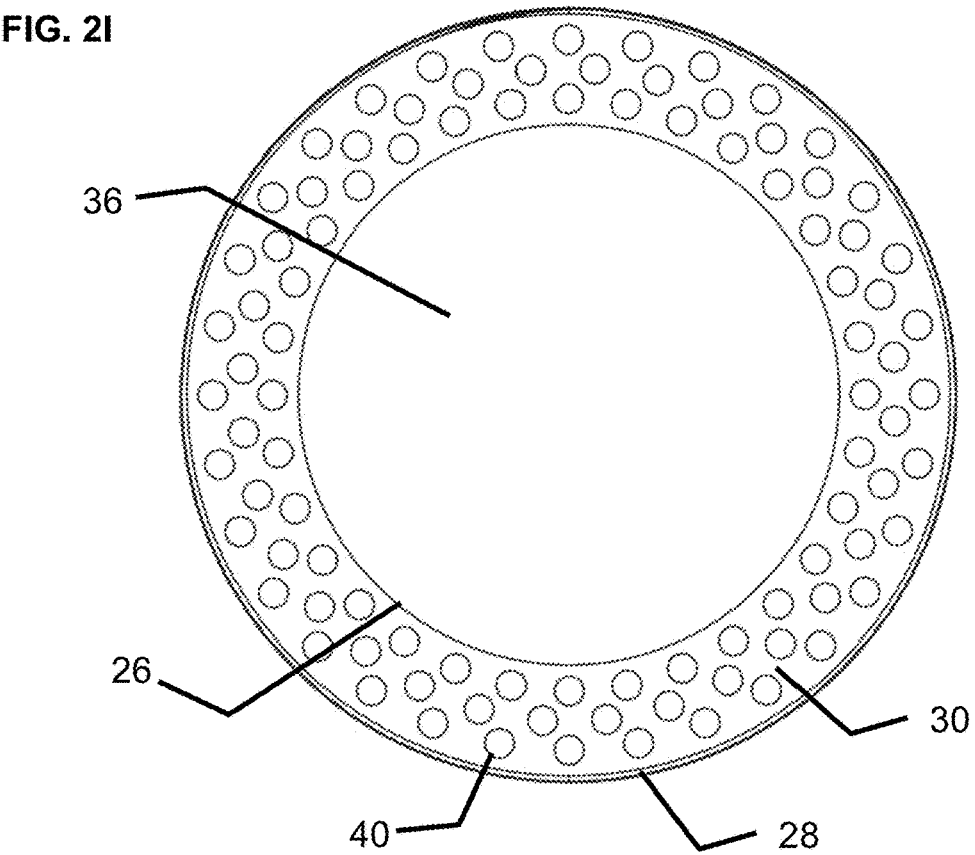
FIG. 2I is a bottom view of the lip of a sixth embodiment of a skin treatment device of the invention, which has cylindrical protrusions on the lip.

In certain alternative embodiments, raised and spaced apart protrusions 40 can be provided on the proximal surface of lip 28 separated by non-linear channels instead of radial channels, as shown in FIG. 2I. Protrusions 40 selectively: (i) permit air and a portion of water applied to the skin with the skin treatment device to escape from the chamber through channels 30 as protrusions 40 and channels 30 are initially compressed against the skin until a seal is formed between lip 28 and skin 48; and (ii) permit air to enter the chamber upon decompression of the lip 28, protrusions 40 and channels 30 to break the seal between lip 28 and skin 48. The pathways for the passage of water and air between protrusions 40 of FIG. 2I are circuitous unlike the linear and radial channels 30 defined by the protrusions 40 of FIGS. 2B, 2C and 2F.

Protrusions can be provided in a wide variety of shapes and sizes. The particular shapes can be selected to achieve the desired flow of water and air during use of the device. Suitable shapes include but are not limited to cylinders with rounded or flat ends (as shown in FIG. 2I), hemispheres, spheres, spheroids, cubes, cuboids, rectangular prisms, pyramids and other regular or irregular shapes. The top surfaces of the protrusions can be, e.g., flat (as in the embodiment of FIG. 2B, arched (as in the embodiment of FIG. 2C, which is identical to the embodiment of FIG. 2B except for the difference in the top surfaces of the respective protrusions 40), rounded, pointed, slanted or irregular.

Each channel 30 preferably has the following dimensions.

The depth of the channels is preferably 0.1 mm to 5 mm, or 0.25 mm to 2.0 mm, or 0.40 mm to 0.60 mm. The depth is measured from a plane defined by the areas of the proximal surface of the lip between channels or protrusions. In embodiments where there is no space between the channels and the adjacent protrusions (see, e.g., FIG. 1D), the depth is measured from the midpoint of distance between the bottom of the channels to the top of the protrusions.

The width of the channels preferably narrows from the outside of the lip to the inside of the lip. The innermost width of the channels is preferably 0.1 mm to 5 mm, or 0.75 mm to 4 mm, or 2 mm to 3.5 mm. The outermost width of the channels is preferably 0.1 mm to 10 mm, or 0.75 mm to 7.5 mm, or 2.5 mm to 5.0 mm.

The channels preferably traverse the entirety of the lip from inside to outside. The channels preferably have a length of 1 mm to 15 mm, or 5 mm to 12 mm, or 7 mm to 10 mm.

In preferred embodiments, each end of channels 30 has an internal perimeter wall 44 and an external perimeter wall 42. The height of each of these walls may be, e.g., 10, 20, 30, 40, 50, 60, 70, 80, 90, 100, 110, 125, 150, or more percent of the depth of the channel. Thus, for example, if the depth of the channel is 0.25 mm, an internal perimeter wall and an external perimeter wall rising from the top of the channel by 0.25 mm, would have a height that is 100% of the depth of the channel. In this example, the top of perimeter walls would be 0.5 mm above the bottom of the channel.

Referring to FIGS. 1H-1K, as device 20 is compressed against skin 48, protrusions 40 and channels 30 are progressively compressed until internal perimeter walls 44 and external perimeter walls 42 contact skin 48, substantially sealing each channel 30, to form multiple sealed compartments around lip 28. These sealed compartments function like suction cups, and increase the amount of force necessary to remove the device from the skin.

In embodiments wherein protrusions and channels are provided on the surface of the lip (see, e.g., FIG. 1C), the protrusions have a preferred height of 0.1 mm to 2.0 mm, or 0.25 mm to 1.75 mm, or 1.00 mm to 1.50 mm, and a preferred width of 1.0 mm to 5.0 mm or 2.5 mm to 4.0 mm. The height is measured from a plane defined by the areas of the proximal surface of the lip between channels or protrusions. In embodiments where there is no space between the channels and the adjacent protrusions (see, e.g., FIG. 1D), the height is measured from the midpoint of distance between the bottom of the channels to the top of the protrusions.

In embodiments wherein protrusions are provided on an otherwise planar lip surface (see, e.g., FIG. 2I), each raised protrusion preferably is cylindrical or conical having a preferred height as measured from proximal surface of the lip of 0.1 mm to 2.0 mm, or 0.25 mm to 1.75 mm, or 1.00 mm to 1.50 mm, and a preferred diameter of 0.5 mm to 5 mm, or 1 mm to 3 mm, or 1.75 mm to 2.25 mm. The protrusions are preferably separated from each other by a distance of 0.5 mm to 5 mm, or 1 mm to 3 mm, or 1.75 mm to 2.25 mm.

The protrusions are preferably provided in a quantity sufficient to completely cover the proximal surface of the lip other than the channels. In other embodiments, 10-100% or 25-75% of the proximal surface of the lip is free of protrusions and channels.

Figure 14A:
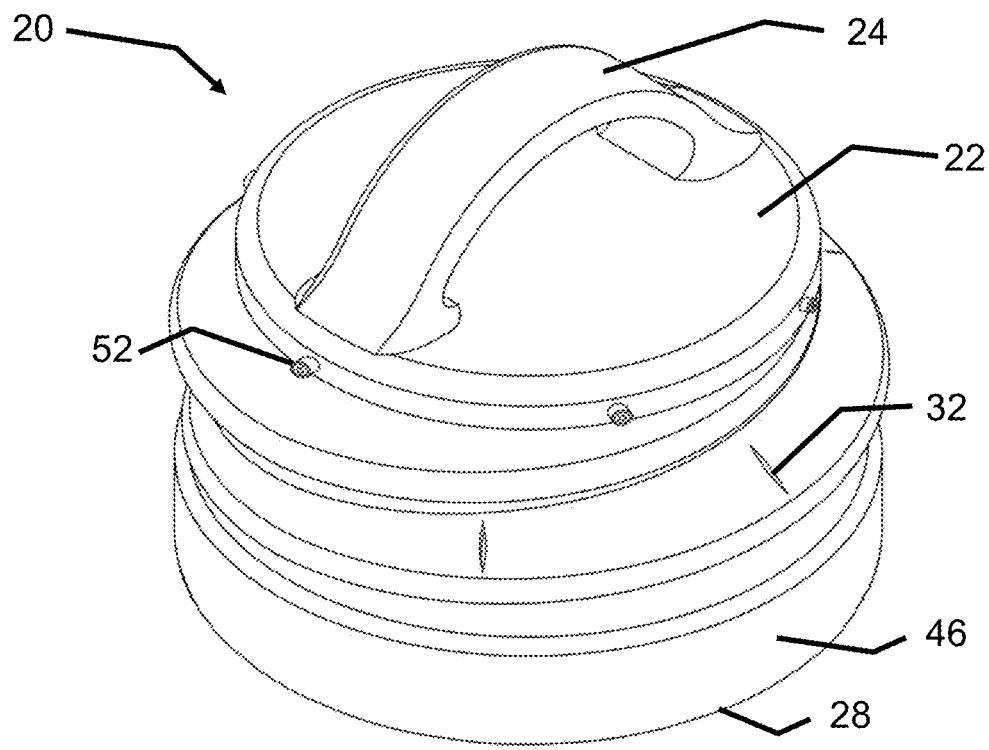
FIG. 14A is a front isometric view of a tenth embodiment of a skin treatment device of the invention.
Figure 14:
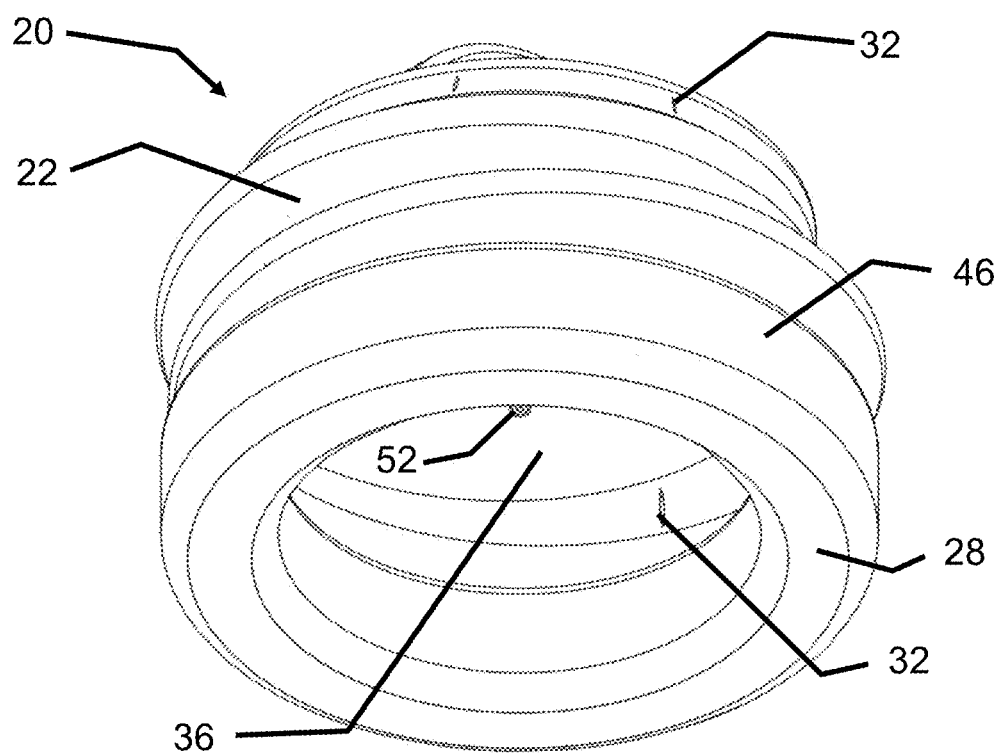
FIG. 14B is a back bottom isometric view of the skin treatment device shown in FIG. 14A.

FIGS. 14A and 14B show an embodiment of device 20 in which lip 28 is free of protrusions and channels. Inlet valves 52 are provided through enclosure to selectively permit air to enter chamber 36 during decompression of device 20. Inlet valves are preferably located far enough away from the proximal end of device 20 so that they are not covered over by enclosure 20 during compression of device 20. Inlet valves 52 are preferably one-way valves configured to permit air to enter chamber 36 only during decompression to assist with breaking the seal between lip 28 and skin 48. Inlet valves 52 are selected to (or can be adjusted to) admit air to chamber 36 only upon reaching a desired cracking pressure (i.e., a minimum air pressure differential between the air in device 20 and ambient air pressure outside device 20 required to initiate the flow of air through inlet valves 52), so as to regulate the amount of suction that can be applied by decompression of device 20 before the seal between lip 28 and skin 48 is broken.

A plurality of inlet valves 52 are preferably spaced apart about the perimeter of enclosure 22. The number of inlet valves 52 is preferably 1, 2, 3, 4, 5, 6, 7, 8, 9, 10 or more. Inlet valves 52 of a given device may have the same cracking pressure, or may have different cracking pressures so that air is admitted to chamber 36 in different stages of decompression. Although inlet valves 52 are illustrated only with respect to an embodiment in which the proximal surface of lip 28 is free of protrusions and channels, inlet valves can also be provided in embodiments of the device wherein less than 100% of the proximal surface of lip is free of protrusions and channels. It is also within the scope of the invention to include two-way valves instead of, or in addition to, the inlet valves and/or outlet valves. Such two-way valves function as outlet valves during compression and as inlet valves during decompression.

Enclosure 22 and lip 28 preferably have a transverse cross-section (i.e., a cross-section perpendicular to the longitudinal axis of the device) that is circular or ovular. The outside wall of lip 28 is preferably convex rather than flat, has a smooth external surface (e.g., free of protrusions and channels), and tapers inwardly in a proximal direction such that the smooth external surface is configured to contact the skin as the skin treatment device is compressed so as to form an outermost circumference of the seal formed between the lip and the skin when the protrusions and the channels of the proximal surface of the lip are fully compressed against the skin (i.e., compressed to the extent necessary to form the seal).

Certain embodiments of skin treatment devices of the invention are sized to fit comfortably in or on the hand of a user. Other embodiments are sized to treat smaller areas of the skin (e.g., fingers, sides of the nose, etc.) and may be approximately the size of a sewing thimble. Thus, e.g., certain embodiments of the skin treatment devices may have a maximum diameter of 6.35 mm to 100 mm and a maximum height of 6.35 mm to 100 mm.

The skin treatment device can further comprise a motor, a control button and control electronics configured to repeatedly compress the enclosure, seal the lip to the skin being treated, decompress the enclosure, break the seal and remove the device from the skin. Suitable motors and mechanisms for the device can be adapted from those disclosed in, e.g., US20160022009A1, U.S. Pat. No. 8,518,001B2, U.S. Pat. No. 4,114,781A and US20140323993A1.

Skin Treatment Method

The method of the invention comprises providing a volume of water in enclosure 22 for subsequent application to the skin of the subject to be treated for a disorder, such as dermatitis or psoriasis. The volume of water is preferably at least 1 ml and no more than 250 ml, more preferably from 1.5 to 100 ml, and still more preferably from 10 to 50 ml. In a preferred embodiment, water is captured from a stream of water, such as from a shower head or sink faucet, as device 20 is manually passed through the stream on its way toward the targeted skin of the user. The initial water-capturing and skin-contacting motion mimics a gentle slapping of the skin to be treated.

As lip 28 is placed in contact with the skin with the water in enclosure 22, force is selectively applied to enclosure 22 to press lip 28 and protrusions 40 against the surface of the skin to be treated and to compress enclosure 22. The compression force is terminated when the seal between lip 28 and skin 48 is formed, and then decompression force is applied to decompress enclosure 22, lip 28, channels 30 and protrusions 40 to break the seal and release device 20 from the skin, such that water is released from enclosure 22. This is deemed a single treatment cycle.

The treatment cycle is repeated at least once. In certain embodiments, the treatment cycle is repeated for each area of the skin to be treated 1-100 times or 5-75 times or 10-25 times. The rate at which the cycles are repeated may vary depending on the dexterity of the user of device 20, but preferably treatment is conducted at a rate of 30-180 or 60-120 cycles per minute.

The amount of force applied to compress enclosure 22 is preferably from 0.44 N to 44 N, more preferably from 5 N to 30 N, or still more preferably from 10 N to 25 N. The amount of decompression force applied to decompress enclosure 22 is preferably from −0.45 N to −45 N, more preferably from −5 N to −30 N, or still more preferably from −10 N to −25 N. It is preferred that the decompression force be greater than the compression force.

In certain embodiments, the air pressure measured within the chamber ranges from 0-7 psi (0-48.3 kPa) as the device is being fully compressed. Preferably, the air pressure is 2.5-4.5 psi (17.2-31.0 Pascal) under such conditions.

The water to be applied to the skin is preferably very warm to comfortably hot to the touch. For example, the water temperature is 36.7° C. to 41.1° C., or 38.9° C. to 40° C. Such higher temperature water makes the skin more supple and helps dilute and/or wash away the skin's exudates. The use of high temperature water is surprisingly effective for use in treating eczema, for which hot water is conventionally understood to be contraindicated.

The method is effective for treating skin conditions, including but not limited to inflammatory skin conditions such as psoriasis, eczema and other forms of dermatitis as well as common forms of acne.

Device 20 is used to administer a treatment of the invention to the skin of the user and/or to the skin of an individual other than the user. The individual to be treated can be any animal, or any mammal, and preferably is a human.

The invention will be illustrated in more detail with reference to the following Examples, but it should be understood that the present invention is not deemed to be limited thereto.

EXAMPLES

Example 1—Dermatitis

Figure 3A:
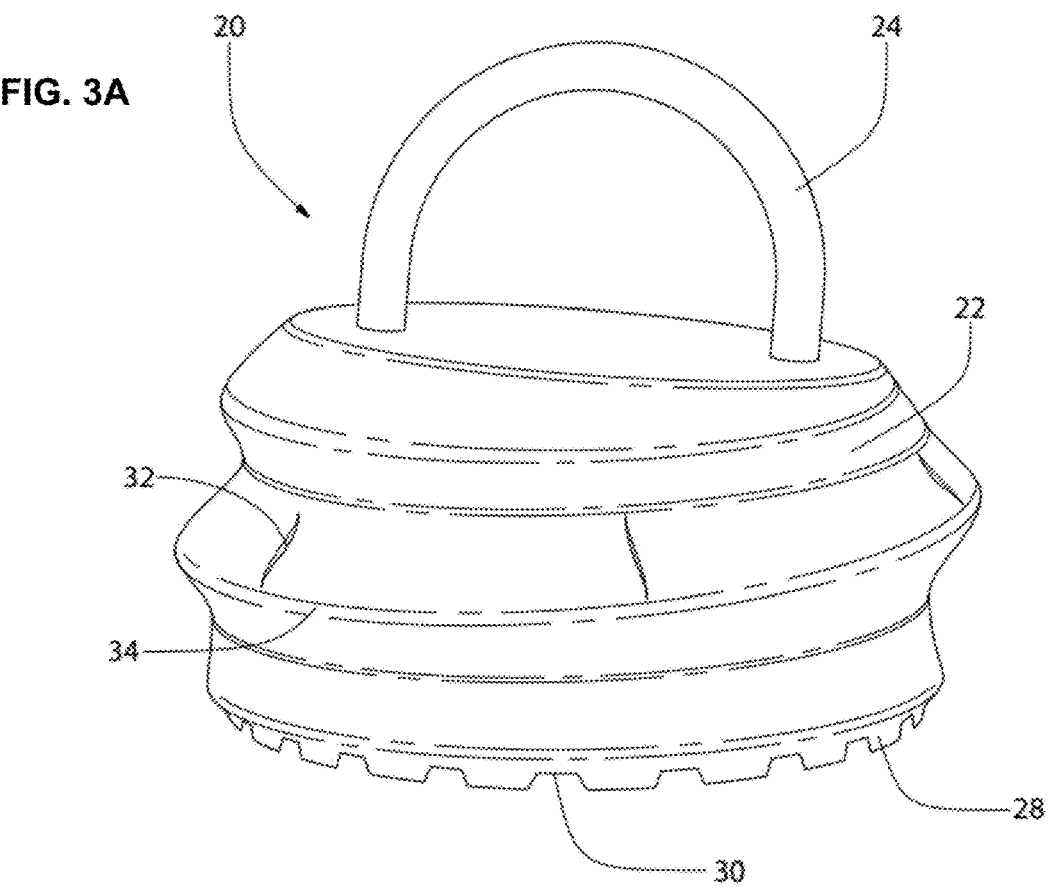
FIG. 3A is a front perspective view of a seventh embodiment of a skin treatment device of the invention.
Figure 3B:
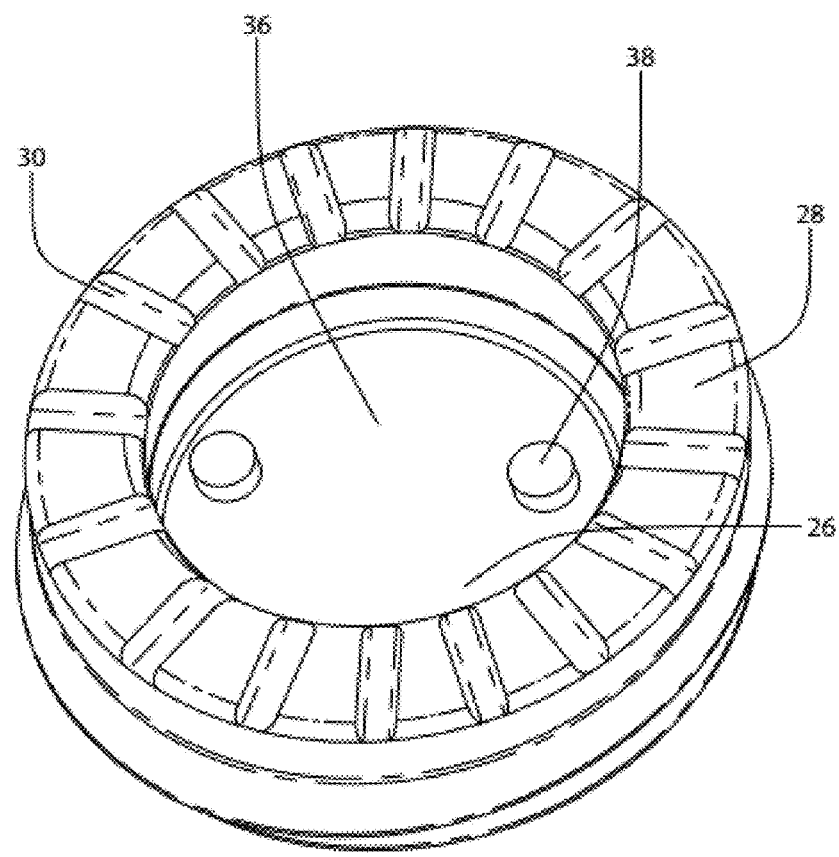
FIG. 3B is a bottom perspective view of the skin treatment device shown in FIG. 3A.

A 31-year-old Caucasian female (Subject 1) suffering from perioral dermatitis treated her face using a device 20, which was a version of the device of FIG. 3A but with a less refined version of the lip of FIG. 1C. Volumes of water at a temperature of about 38 to 41° C. were applied to the face with manual force. The volumes of water in the device were administered serially with a fresh volume of water being applied to the face of Subject 1 after the volume of water had been depleted in the preceding cycle. The volume of water applied in each administration cycle was about 10-15 ml. The device was manually depressed against the skin to adhere the device to the skin by suction. Compression force was terminated and decompression (i.e., pulling) force against the elastic strap was initiated to decompress the device and pull it off the skin. The compression force applied to adhere the device to the skin was about 0.1-5 lbf (0.44-22

N) per cycle. The decompression force used to overcome the vacuum and remove the device from the skin was of a magnitude greater than the compression force (i.e., −0.45 to −23 N). The duration of each cycle was about 0.25 to 1 second. The water temperature was about 102-106 F (38.9-41.1 C). Treatment cycles were repeated about 10 times on each area of skin to be treated. Subject 1 had about 10-12 different areas on her face that were treated in this manner twice a day (morning and night). In addition, Subject 1 followed each treatment by applying a moisturizer (e.g., CERAVE Daily Moisturizing Lotion, L'Oreal S.A., France) to the treated areas of the skin with gentle pressure, facilitating penetration into the epidermal layers and promoting hydration.

Figure 6A:
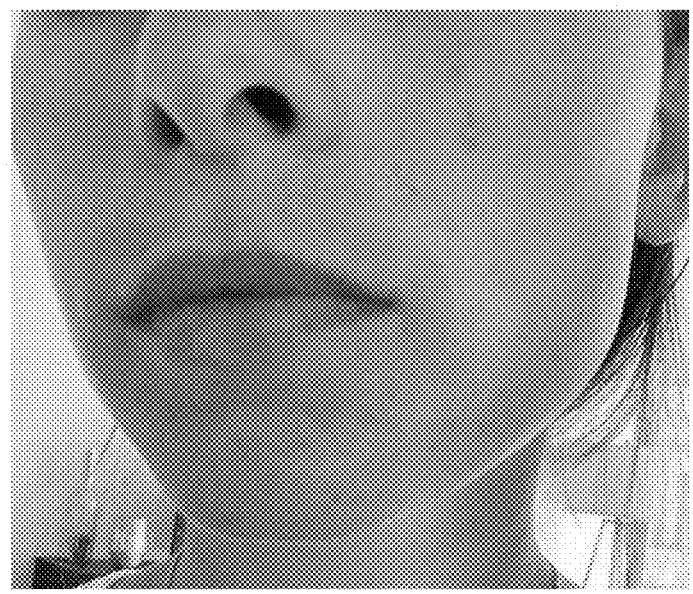
FIG. 6A is a pre-treatment photograph of the face of Subject 1 of Example 1.
Figure 6B:
FIG. 6B is another pre-treatment photograph of the face of Subject 1.
Figure 6C:
FIG. 6C is a photograph of the face of Subject 1 after one week of treatment.

FIGS. 6A and 6B are photographs of the face of Subject 1 before starting the treatment. Inflammation and flaking surrounding the mouth of Subject 1 are readily apparent. Inflammation to the right of the right nostril and red pimples are also apparent. FIG. 6C is a photograph of the face of Subject 1 after one week of treatment. The post-treatment photo demonstrates marked improvement of the skin condition of Subject 1. The red discoloration has largely faded from her face. No flakes of skin or scaling are visible. After five weeks of treatment, the skin of Subject 1 has maintained its healthy appearance without further treatments. Thus, the skin disorder appears to be in remission.

Example 2—Atopic Dermatitis

A 16-year-old Caucasian male (Subject 2) suffering from atopic dermatitis treated the top of his foot using the same method as used in Example 1. FIG. 7A is a pre-treatment photograph of the foot of Subject 2 showing signs of significant inflammation, including thickened, scaly and flaky skin patches. FIG. 7B shows the foot after 1 week of treatment. FIG. 7C shows the foot after 3 weeks of treatment. Signs of inflammation were significantly reduced after 1 week and nearly gone after 3 weeks. After 4 weeks of treatment, the foot of Subject 2 appeared free of the condition. The foot of Subject 2 has maintained its healthy appearance without further treatments, such that the condition appears to be in remission.

Example 3—Acne

A 20-year-old Caucasian male (Subject 3) suffering from acne treated his forehead using the same method as used in Example 1. FIG. 8A is a pre-treatment photograph of the forehead of Subject 3 in which blackheads, whiteheads and inflammation are visible. Blemishes (numbered 1, 2 and 3) and signs of inflammation were significantly reduced after 1 week, as shown in FIG. 8B.

Example 4—Psoriasis

Figure 9D:
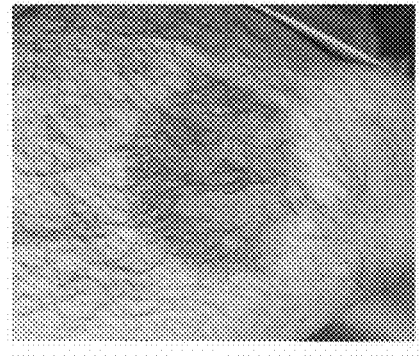
FIG. 9D is a photograph of the forearm of Subject 4 after two weeks of treatment.
Figure 9C:
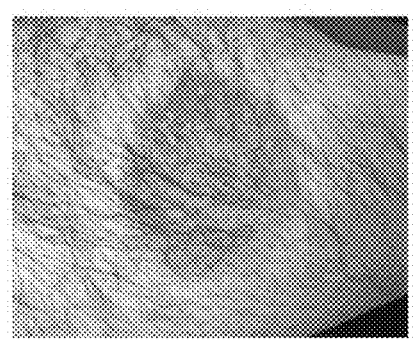
FIG. 9C is a photograph of the forearm of Subject 4 after three days of treatment.
Figure 9B:
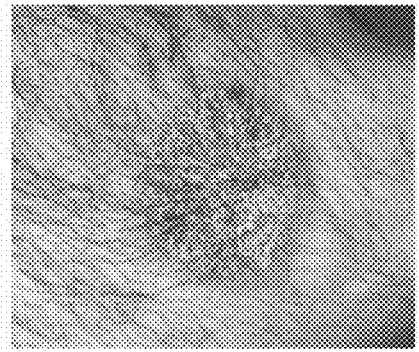
FIG. 9B is a photograph of the forearm of Subject 4 after one day of treatment.
Figure 9A:
FIG. 9A is a pre-treatment photograph of the forearm of Subject 4 of Example 4.
Figure 9H:
FIG. 9H is a photograph of the forearm of Subject 4 after sixteen weeks of treatment.
Figure 9G:
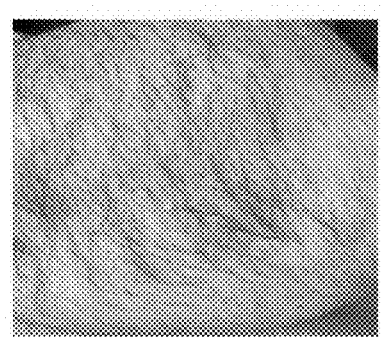
FIG. 9G is a photograph of the forearm of Subject 4 after eleven weeks of treatment.
Figure 9F:
FIG. 9F is a photograph of the forearm of Subject 4 after eight weeks of treatment.
Figure 9E:
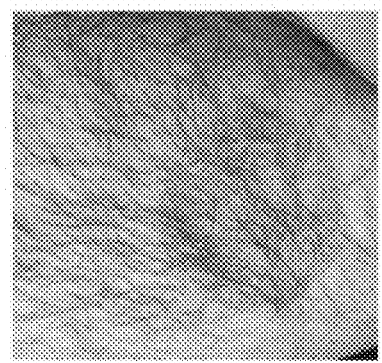
FIG. 9E is a photograph of the forearm of Subject 4 after six weeks of treatment.
Figure 10A:
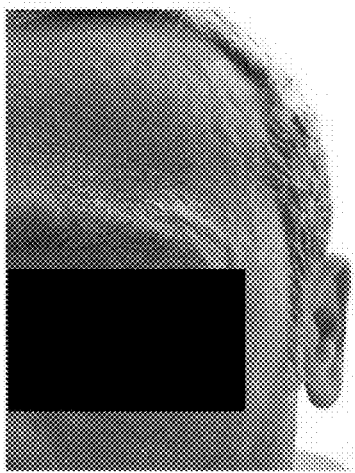
FIG. 10A is a pre-treatment photograph of an eyebrow of Subject 5 of Example 5.
Figure 10B:
FIG. 10B is a pre-treatment photograph of the lower cheek of Subject 5.
Figure 10C:
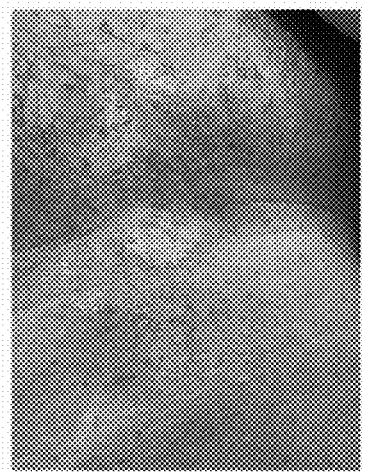
FIG. 10C is a pre-treatment photograph of the chest of Subject 5.
Figure 10D:
FIG. 10D is a photograph of the eyebrow of Subject 5 after two months of treatment.
Figure 10E:
FIG. 10E is a photograph of the lower cheek of Subject 5 after two months of treatment.
Figure 10F:
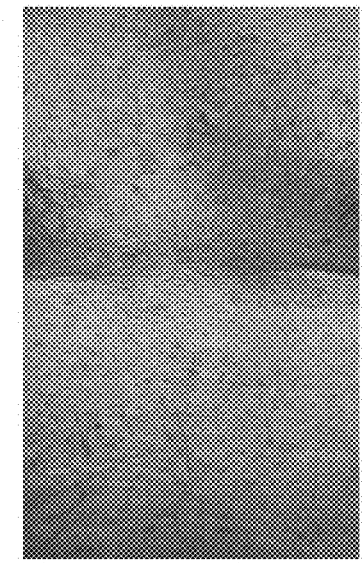
FIG. 10F is a photograph of the chest of Subject 5 after two months of treatment.
Figure 11A:
FIG. 11A is a pre-treatment photograph of a sideburn of Subject 5.
Figure 11B:
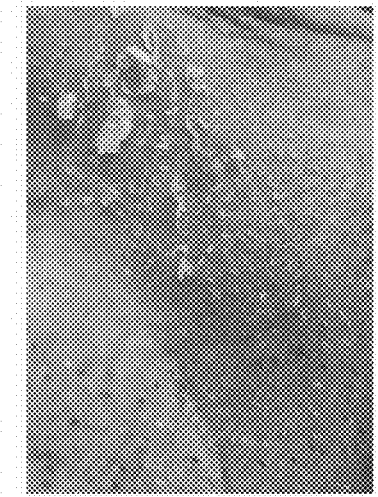
FIG. 11B is a pre-treatment photograph of the mid-cheek of Subject 5.
Figure 11C:
FIG. 11C is a pre-treatment photograph of the mid-cheek of Subject 5.
Figure 11D:
FIG. 11D is a photograph of the sideburn of Subject 5 after two months of treatment.
Figure 11E:
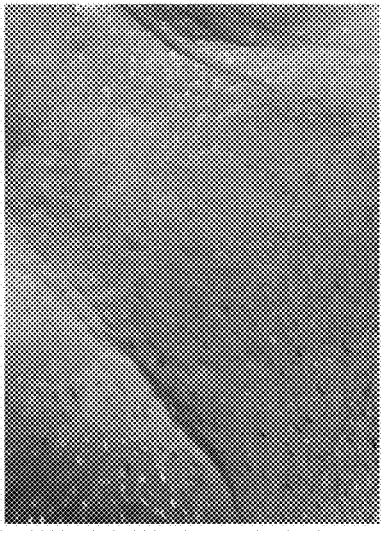
FIG. 11E is a photograph of the mid-cheek of Subject 5 after two months of treatment.
Figure 11F:
FIG. 11F is a photograph of the mid-cheek of Subject 5 after two months of treatment.

A 40-year-old Caucasian male (Subject 4) suffering from psoriasis treated his forearm using the same method as used in Example 1, except that he treated himself three times per day rather than two times per day. FIG. 9A is a pre-treatment photograph of the forearm of Subject 4 showing significant signs of psoriasis, including large plaques. FIGS. 9B-9H track the progress of treatment over sixteen weeks. After sixteen weeks of treatment, the plaques were largely eliminated, as shown in FIG. 9H. No treatment was conducted after sixteen weeks, but the condition continued to improve for the next six weeks post-treatment, such that the condition appears to be in remission.

Example 5—Seborrheic Dermatitis

A 57-year-old Caucasian male (Subject 5) suffering from seborrheic dermatitis on his head and chest was treated using the same method as used in Example 1. FIGS. 10A, 10B, 10C, 11A, 11B and 11C are pre-treatment photos of Subject 5. FIGS. 10D, 10E, 10F, 11D, 11E and 11F are photos taken after prolonged use of the device. The condition of the skin improved within about two months of commencing treatment. Continued use of the device has maintained the healthy condition of the skin as shown in the after figures, such that the seborrheic dermatitis appears to be in remission.

Example 6—Eczema

Figure 12A:
FIG. 12A is a pre-treatment photograph of the back of Subject 6 of Example 6.
Figure 12B:
FIG. 12B is a photograph of the back of Subject 6 after two months of treatment.

A 60-year-old Caucasian male (Subject 6) suffering from eczema on his back, which presented as flaky, inflamed, itchy skin. He was treated using the same method as used in Example 1. Subject 6 felt immediate itch relief after his first treatment with the inventive device. FIG. 12A is a pre-treatment photo of Subject 6. FIG. 12B is a photo taken after two weeks of using the device, at which time the skin appeared healthy. Sporadic use of the device since that time has maintained the healthy condition of the skin, such that the eczema appears to be in remission.

Example 7—Eczema

Figure 13A:
FIG. 13A is a pre-treatment photograph of the upper right arm of Subject 7 of Example 7.
Figure 13A:
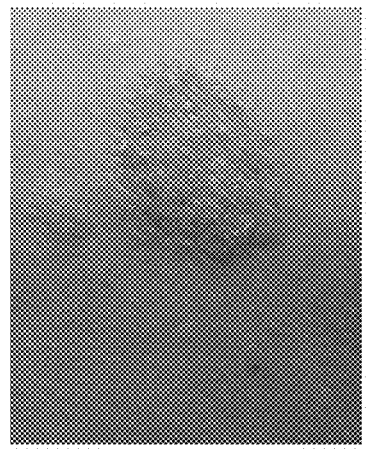
Figure 13A:
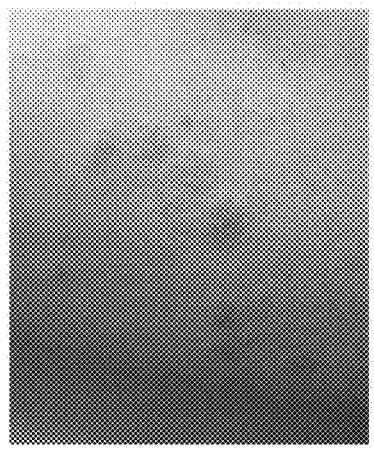
Figure 13A:
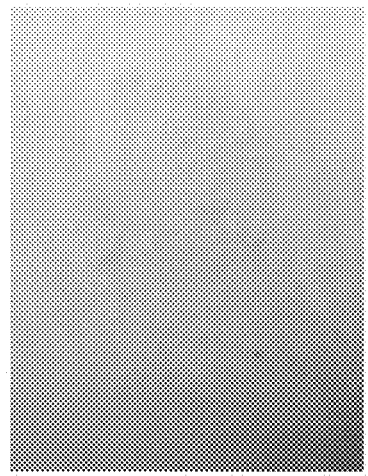
Figure 13A:

A 31-year-old Caucasian female (Subject 7) was suffering from eczema on her upper arm, which presented as flaky, inflamed, itchy skin. See the pre-treatment photos of her upper arm (FIG. 13A), and the close-up photos of the largest lesion (FIG. 13B) and the cluster of lesions (FIG. 13C) also visible in FIG. 13A. The upper arm of Subject 7 was treated using the same method as used in Example 1. Subject 7 felt immediate itch relief after her first treatment with the inventive device. After two weeks of treatment, the flakiness and inflamed skin were largely eliminated, as shown in FIGS. 13D and 13E, which show the same areas of skin as FIG. 13B and FIG. 13C, respectively. Sporadic treatment continued for the two weeks following the two week treatment period with the condition continuing to improve, such that the condition appears to be in remission with no further treatment with the device.

Achieving the results described in the above Examples using water without any medicaments or cleaning agents was surprising. No side effects from using the device were noted.

ADDITIONAL NUMBERED EMBODIMENTS OF THE INVENTION

What follows is a non-exhaustive list of embodiments of the invention.
  1. A skin treatment device for treating skin comprising:
    an enclosure configured to selectively admit and expel air and water, said enclosure comprising a distal end, a proximal end and a hollow center defining a chamber closed at the distal end and having an opening at the proximal end, wherein the enclosure has sufficient elasticity for repeated compression and decompression along a longitudinal axis thereof;
    a lip provided around a perimeter of the opening at the proximal end of the enclosure, and having sufficient elasticity for repeated compression and decompression;

protrusions and channels on a proximal surface of the lip, wherein the protrusions and channels have sufficient elasticity for repeated compression and decompression and are configured to selectively: (i) permit a flow of air and water to be expelled from the chamber of the enclosure through the channels as the skin treatment device is initially compressed against the skin; (ii) terminate the flow of air and water from the chamber when the lip, protrusions and channels have been sufficiently compressed against the skin to form a seal between the lip and the skin; and (iii) permit air to enter the chamber through the channels when the seal is broken by decompression of the lip, protrusions and channels upon decompression of the device; and at least one outlet valve on the enclosure which is configured to permit an additional flow of air and water out of the chamber to regulate pressure as the enclosure is being compressed against the skin, and to resist admission of air or water into the chamber as the enclosure is being decompressed.

2. The skin treatment device of embodiment 1, wherein the channels comprise external perimeter walls and internal perimeter walls, which have a height less than a height of the protrusions such that upon compression of the protrusions against the skin, the external perimeter walls and the internal perimeter walls are configured to contact the skin to seal the channels and provide a plurality of sealed compartments around the lip, and wherein the sealed compartments are configured to apply suction to the skin as the device is decompressed and increase an amount of decompression force required to remove the device from the skin.

3. The skin treatment device of embodiment 1 or 2, further comprising: (a) a strap on the distal end of the enclosure and configured to receive and removably retain at least a portion of a hand of a user of the skin treatment device; or (b) a handle shaped and sized to be gripped by a human hand and extending distally from the distal end of the enclosure.

4. The skin treatment device of embodiment 3, which includes the strap, wherein the strap is configured to receive at least one finger of the user and possesses elasticity.

5. The skin treatment device of any one of embodiments 1-4, wherein the enclosure and the lip comprise a material independently selected from the group consisting of silicone, silicone rubber, rubber, neoprene, polyurethane, nitrile rubber, butyl rubber, chlorosulfonated polyethylene, ethylene propylene diene monomer, styrene-butadiene rubber, ethylene propylene diene monomer, chloroprene rubber, fluoroelastomer, acrylonitrile butadiene rubber, polybutadiene rubber, polyisoprene rubber, styrene-isoprene-styrene block copolymer, and styrene-butadiene-styrene block copolymer.

6. The skin treatment device of embodiment 5, wherein the lip is more flexible than the enclosure, has a convex circumferential wall with a smooth external surface and tapers inwardly in a proximal direction such that the smooth external surface is configured to contact the skin as the skin treatment device is compressed so as to form an outermost circumference of the seal formed between the lip and the skin when the protrusions and the channels of the proximal surface of the lip are fully compressed against the skin.

7. The skin treatment device of any one of embodiments 1-6, further comprising at least one spring housed within the enclosure and configured to provide resistance against the device being compressed against the skin.

8. The skin treatment device of embodiment 7, wherein the at least one spring is a helical spring configured to be compressed to its solid height by applying a force within a range from 0.44 N to 44 N.

9. The skin treatment device of any one of embodiments 1-8, wherein the enclosure is sufficiently resilient to provide a spring-like effect and the skin treatment device is free of a separate spring.

10. The skin treatment device of any one of embodiments 1-9, wherein the at least one outlet valve comprises a resealable slit through the enclosure.

11. The skin treatment device of any one of embodiments 1-10, wherein the enclosure and the lip have a circular, elliptical or kidney-shaped transverse cross-section.

12. The skin treatment device of any one of embodiments 1-11, wherein the channels fully extended radially across the proximal surface of the lip.

13. The skin treatment device of any one of embodiments 1-12, further comprising a motor, a control button and control electronics configured to repeatedly compress and decompress the enclosure to repeatedly form and break the seal between the lip and the skin.

14. The skin treatment device of any one of embodiments 1-13, wherein the protrusions are configured to expand to initiate breaking of the seal upon the decompression of the device.

15. The skin treatment device of any one of embodiments 1-14, which is sufficiently flexible to conform to contours and crevices of the skin.

16. A method for treating a skin disorder, said method comprising the following steps:
(a) providing the skin treatment device of any one of embodiments 1-15;
(b) providing a volume of water in the chamber;
(c) placing the lip in contact with the skin;
(d) compressing the enclosure against the skin by applying an amount of compression force so as to apply the water in the chamber to the skin;
(e) terminating the compressing when the seal between the lip and the skin is formed, to provide an internal air pressure in the chamber of the device less than an ambient air pressure outside the device;
(f) pulling the enclosure away from the skin to decompress the enclosure, generate suction to draw water and debris away from the skin, decompress the protrusions, channels and lip to break the seal between the lip and the skin, and remove the enclosure from the skin;
(g) allowing at least some of the volume of water remaining in the chamber to drain out; and
(h) repeating steps (b) through (g) at least once.

17. The method of embodiment 16, wherein step (h) is repeated 9-15 times for each area of skin to be treated.

18. The method of embodiment 16 or 17, wherein the skin disorder is psoriasis, dermatitis, acne or eczema.

19. The method of any one of embodiments 16-18, wherein the volume of water in each iteration of step (b) is 1-250 ml, a temperature of the water is 36.7° C. to 41.1° C., and cycles consisting of steps (b) through (g) are conducted at a rate of 30-180 cycles per minute.

20. The method of embodiment 19, wherein the amount of the compression force applied in step (d) of each of the cycles is from 0.44 N to 44 N.

21. The method of embodiment 20, wherein an amount of a decompression force applied in step (e) of each of the cycles is from −0.45 N to −45 N, and is greater than the amount of compression force applied in step (d).
22. The method of any one of embodiments 16-21, which is conducted free of medicaments and free of cleansing agents other than water.
23. The method of any one of embodiments 16-21, further comprising applying a moisturizer to the skin as a final step.
24. The method of any one of embodiments 16-23, wherein the protrusions expand to initiate the breaking of the seal upon the decompression of the device.
25. The method of any one of embodiments 16-24, wherein the device flexibly conforms to contours and crevices of the skin in the compressing step.
26. A skin treatment device for treating skin comprising:
an enclosure configured to selectively admit and expel air and water, said enclosure comprising a distal end, a proximal end and a hollow center defining a chamber closed at the distal end and having an opening at the proximal end, wherein the enclosure has sufficient elasticity for repeated compression and decompression along a longitudinal axis thereof;
a lip provided around a perimeter of the opening at the proximal end of the enclosure, and having sufficient elasticity for repeated compression and decompression;
at least one outlet valve on the enclosure which is configured to selectively: (i) permit a flow of air and water to be expelled from the chamber of the enclosure through the at least one outlet valve as the skin treatment device is initially compressed against the skin; (ii) terminate the flow of air and water from the chamber when the lip has been sufficiently compressed against the skin to form a seal between the lip and the skin; and (iii) resist admission of air or water into the chamber as the enclosure is being decompressed; and
at least one inlet valve configured to permit air to enter the chamber during decompression to break the seal between the lip and the skin.
27. The skin treatment device of embodiment 26, wherein the at least one outlet valve and the at least one inlet valve are the same two-way valve.
28. A method for treating a skin disorder, said method comprising the following steps:
(a) providing the skin treatment device of embodiment 26 or 27;
(b) providing a volume of water in the chamber;
(c) placing the lip in contact with the skin;
(d) compressing the enclosure against the skin by applying an amount of compression force so as to apply the water in the chamber to the skin;
(e) terminating the compressing when the seal between the lip and the skin is formed, to provide an internal air pressure in the chamber of the device less than an ambient air pressure outside the device;
(f) pulling the enclosure away from the skin to decompress the enclosure, generate suction to draw water and debris away from the skin, and remove the enclosure from the skin;
(g) allowing at least some of the volume of water remaining in the chamber to drain out; and
(h) repeating steps (b) through (g) at least once.

The skin treatment device of embodiments 26 or 27, or the method of embodiment 28, having at least one of the features of at least one of embodiments 3-5, 7-11, 13, 15, 17-23 and 25.

While the invention has been described in detail and with reference to specific examples thereof, it will be apparent to one skilled in the art that various changes and modifications can be made therein without departing from the spirit and scope thereof.

LIST OF REFERENCE NUMBERS

20 Device
22 Enclosure
24 Strap
26 Opening
28 Lip
30 Channel
32 Outlet valve
34 Spring
36 Chamber
38 Anchor
40 Protrusion
42 External Perimeter Wall
44 Internal Perimeter Wall
46 Circumferential Wall
48 Skin
50 Handle
52 Inlet valve

What is claimed is:
1. A skin treatment device for treating skin comprising:
an enclosure configured to selectively admit and expel air and water, said enclosure comprising a distal end, a proximal end and a hollow center defining a chamber closed at the distal end and having an opening at the proximal end, wherein the enclosure has sufficient elasticity for repeated compression and decompression along a longitudinal axis thereof;
a lip provided around a perimeter of the opening at the proximal end of the enclosure, and having sufficient elasticity for repeated compression and decompression;
protrusions and channels on a proximal surface of the lip, wherein the protrusions and channels have sufficient elasticity for repeated compression and decompression and are configured to selectively: (i) permit a flow of air and water to be expelled from the chamber of the enclosure through the channels as the skin treatment device is initially compressed against the skin; (ii) terminate the flow of air and water from the chamber when the lip, protrusions and channels have been sufficiently compressed against the skin to form a seal between the lip and the skin; and (iii) permit air to enter the chamber through the channels when the seal is broken by decompression of the lip, protrusions and channels upon decompression of the device; and
at least one outlet valve on the enclosure which is configured to permit an additional flow of air and water out of the chamber to regulate pressure as the enclosure is being compressed against the skin, and to resist admission of air or water into the chamber as the enclosure is being decompressed.
2. The skin treatment device of claim 1, wherein the channels comprise external perimeter walls and internal perimeter walls, which have a height less than a height of the protrusions such that upon compression of the protrusions against the skin, the external perimeter walls and the internal perimeter walls are configured to contact the skin to seal the channels and provide a plurality of sealed compartments around the lip, and wherein the sealed compartments are configured to apply suction to the skin as the device is decompressed and increase an amount of decompression force required to remove the device from the skin.

3. The skin treatment device of claim 1, further comprising: (a) a strap on the distal end of the enclosure and configured to receive and removably retain at least a portion of a hand of a user of the skin treatment device; or (b) a handle shaped and sized to be gripped by a human hand and extending distally from the distal end of the enclosure.

4. The skin treatment device of claim 3, which includes the strap, wherein the strap is configured to receive at least one finger of the user and possesses elasticity.

5. The skin treatment device of claim 1, wherein the enclosure and the lip comprise a material independently selected from the group consisting of silicone, silicone rubber, rubber, neoprene, polyurethane, nitrile rubber, butyl rubber, chlorosulfonated polyethylene, ethylene propylene diene monomer, styrene-butadiene rubber, ethylene propylene diene monomer, chloroprene rubber, fluoroelastomer, acrylonitrile butadiene rubber, polybutadiene rubber, polyisoprene rubber, styrene-isoprene-styrene block copolymer, and styrene-butadiene-styrene block copolymer.

6. The skin treatment device of claim 5, wherein the lip is more flexible than the enclosure, has a convex circumferential wall with a smooth external surface and tapers inwardly in a proximal direction such that the smooth external surface is configured to contact the skin as the skin treatment device is compressed so as to form an outermost circumference of the seal formed between the lip and the skin when the protrusions and the channels of the proximal surface of the lip are fully compressed against the skin.

7. The skin treatment device of claim 1, further comprising at least one spring housed within the enclosure and configured to provide resistance against the device being compressed against the skin.

8. The skin treatment device of claim 7, wherein the at least one spring is a helical spring configured to be compressed to its solid height by applying a force within a range from 0.44 N to 44 N.

9. The skin treatment device of claim 1, wherein the enclosure is sufficiently resilient to provide a spring-like effect and the skin treatment device is free of a separate spring.

10. The skin treatment device of claim 1, wherein the at least one outlet valve comprises a resealable slit through the enclosure.

11. The skin treatment device of claim 1, wherein the enclosure and the lip have a circular, elliptical or kidney-shaped transverse cross-section.

12. The skin treatment device of claim 1, wherein the channels fully extended radially across the proximal surface of the lip.

13. The skin treatment device of claim 1, further comprising a motor, a control button and control electronics configured to repeatedly compress and decompress the enclosure to repeatedly form and break the seal between the lip and the skin.

14. The skin treatment device of claim 1, wherein the protrusions are configured to expand to initiate breaking of the seal upon the decompression of the device.

15. The skin treatment device of claim 1, which is sufficiently flexible to conform to contours and crevices of the skin.

16. A method for treating a skin disorder, said method comprising the following steps:
(a) providing the skin treatment device of claim 1;
(b) providing a volume of water in the chamber;
(c) placing the lip in contact with the skin;
(d) compressing the enclosure against the skin by applying an amount of compression force so as to apply the water in the chamber to the skin;
(e) terminating the compressing when the seal between the lip and the skin is formed, to provide an internal air pressure in the chamber of the device less than an ambient air pressure outside the device;
(f) pulling the enclosure away from the skin to decompress the enclosure, generate suction to draw water and debris away from the skin, decompress the protrusions, channels and lip to break the seal between the lip and the skin, and remove the enclosure from the skin;
(g) allowing at least some of the volume of water remaining in the chamber to drain out; and
(h) repeating steps (b) through (g) at least once.

17. The method of claim 16, wherein step (h) is repeated 9-15 times for each area of skin to be treated.

18. The method of claim 16, wherein the skin disorder is psoriasis, dermatitis, acne or eczema.

19. The method of claim 16, wherein the volume of water in each iteration of step (b) is 1-250 ml, a temperature of the water is 36.7° C. to 41.1° C., and cycles consisting of steps (b) through (g) are conducted at a rate of 30-180 cycles per minute.

20. The method of claim 19, wherein the amount of the compression force applied in step (d) of each of the cycles is from 0.44 N to 44 N.

21. The method of claim 20, wherein an amount of a decompression force applied in step (e) of each of the cycles is from −0.45 N to −45 N, and is greater than the amount of compression force applied in step (d).

22. The method of claim 16, which is conducted free of medicaments and free of cleansing agents other than water.

23. The method of claim 16, further comprising applying a moisturizer to the skin as a final step.

24. The method of claim 16, wherein the protrusions expand to initiate the breaking of the seal upon the decompression of the device.

25. The method of claim 16, wherein the device flexibly conforms to contours and crevices of the skin in the compressing step.

26. A skin treatment device for treating skin comprising:
an enclosure configured to selectively admit and expel air and water, said enclosure comprising a distal end, a proximal end and a hollow center defining a chamber closed at the distal end and having an opening at the proximal end, wherein the enclosure has sufficient elasticity for repeated compression and decompression along a longitudinal axis thereof;
a lip provided around a perimeter of the opening at the proximal end of the enclosure, and having sufficient elasticity for repeated compression and decompression;
at least one outlet valve on the enclosure which is configured to selectively: (i) permit a flow of air and water to be expelled from the chamber of the enclosure through the at least one outlet valve as the skin treatment device is initially compressed against the skin; (ii) terminate the flow of air and water from the chamber when the lip has been sufficiently compressed against the skin to form a seal between the lip and the skin; and (iii) resist admission of air or water into the chamber as the enclosure is being decompressed; and
at least one inlet valve configured to permit air to enter the chamber during decompression to break the seal between the lip and the skin.

27. The skin treatment device of claim 26, wherein the at least one outlet valve and the at least one inlet valve are the same two-way valve.

28. A method for treating a skin disorder, said method comprising the following steps:
   (a) providing the skin treatment device of claim 26;
   (b) providing a volume of water in the chamber;
   (c) placing the lip in contact with the skin;
   (d) compressing the enclosure against the skin by applying an amount of compression force so as to apply the water in the chamber to the skin;
   (e) terminating the compressing when the seal between the lip and the skin is formed, to provide an internal air pressure in the chamber of the device less than an ambient air pressure outside the device;
   (f) pulling the enclosure away from the skin to decompress the enclosure, generate suction to draw water and debris away from the skin, and remove the enclosure from the skin;
   (g) allowing at least some of the volume of water remaining in the chamber to drain out; and
   (h) repeating steps (b) through (g) at least once.

* * * * *